US007910768B2

(12) United States Patent
Nguyen et al.

(10) Patent No.: US 7,910,768 B2
(45) Date of Patent: Mar. 22, 2011

(54) MATERIALS FOR LITHOGRAPHIC PLATES COATINGS, LITHOGRAPHIC PLATES AND COATINGS CONTAINING SAME, METHODS OF PREPARATION AND USE

(75) Inventors: My T. Nguyen, Kirkland (CA); Marc-Andre Locas, Pierrefonds (CA)

(73) Assignee: American Dye Source, Inc., Baie D'Urfé (CA)

( * ) Notice: Subject to any disclaimer, the term of this patent is extended or adjusted under 35 U.S.C. 154(b) by 489 days.

(21) Appl. No.: 11/746,252

(22) Filed: May 9, 2007

(65) Prior Publication Data
US 2007/0269739 A1    Nov. 22, 2007

Related U.S. Application Data

(60) Provisional application No. 60/747,474, filed on May 17, 2006.

(51) Int. Cl.
*C07C 69/52* (2006.01)
*G03F 7/26* (2006.01)
*B32B 5/16* (2006.01)

(52) U.S. Cl. ............... 560/205; 560/220; 430/270.1; 430/302; 430/281.1

(58) Field of Classification Search .............. None
See application file for complete search history.

(56) References Cited

U.S. PATENT DOCUMENTS

| | | | |
|---|---|---|---|
| 4,517,277 A | 5/1985 | Lynch et al. | |
| 4,701,402 A | 10/1987 | Patel et al. | |
| 5,569,573 A | 10/1996 | Takahashi et al. | |
| 6,008,267 A | 12/1999 | Vallee et al. | |
| 6,124,425 A | 9/2000 | Nguyen | |
| 6,177,182 B1 | 1/2001 | Nguyen | |
| 6,261,740 B1 | 7/2001 | Nguyen et al. | |
| 6,368,772 B1 | 4/2002 | Telser et al. | |
| 6,380,277 B1 | 4/2002 | Oestreich et al. | |
| 6,548,222 B2 | 4/2003 | Teng | |
| 6,566,035 B1 | 5/2003 | Aoshima | |
| 6,582,882 B2 | 6/2003 | Pappas et al. | |
| 6,846,614 B2 | 1/2005 | Timpe et al. | |
| 6,884,560 B2 | 4/2005 | Yanaka et al. | |
| 6,884,562 B1 | 4/2005 | Schadt, III et al. | |
| 6,899,994 B2 | 5/2005 | Huang et al. | |
| 6,960,422 B2 | 11/2005 | Goto | |
| 6,969,575 B2 | 11/2005 | Inno | |
| 6,983,694 B2 | 1/2006 | Vermeersch et al. | |

(Continued)

FOREIGN PATENT DOCUMENTS

| | | |
|---|---|---|
| CA | 1306571 | 8/1992 |
| CA | 2229856 | 9/2000 |
| EP | 0 770 495 A1 | 5/1997 |
| EP | 1 106 639 A1 | 6/2001 |
| EP | 1204000 A1 | 5/2002 |

(Continued)

OTHER PUBLICATIONS

Database CAS citation 1999:626245 [retrieved Dec. 8, 2009] from STN; Columbus, OH, USA.*

*Primary Examiner* — Karl J Puttlitz
(74) *Attorney, Agent, or Firm* — Goudreau Gage Dubuc

(57) ABSTRACT

This invention relates to iodonium salts, acetal copolymers and polymer binders comprising functional groups capable of undergoing cationic or radical polymerization, their method of preparation and their use in the preparation of coating solutions and coatings. This invention also relates to coatings containing the iodonium salts, acetal copolymers and/or polymer binders and to negative working lithographic printing plates comprising these coatings.

30 Claims, 25 Drawing Sheets

U.S. PATENT DOCUMENTS

| | | |
|---|---|---|
| 7,001,704 B2 | 2/2006 | Oshima et al. |
| 7,041,711 B2 | 5/2006 | Kunita |
| 7,279,263 B2 | 10/2007 | Goodin |
| 7,473,515 B2 | 1/2009 | Nguyen et al. |
| 2002/0015826 A1 | 2/2002 | Desmarteau et al. |
| 2003/0162123 A1 | 8/2003 | Barr et al. |
| 2005/0123853 A1 | 6/2005 | Munnelly et al. |
| 2005/0170286 A1 | 8/2005 | Huang et al. |
| 2006/0032390 A1 | 2/2006 | Hoshi et al. |
| 2006/0275698 A1 | 12/2006 | Nguyen et al. |
| 2007/0269727 A1 | 11/2007 | Savariar-Hauck et al. |
| 2008/0229957 A1 | 9/2008 | Yu |
| 2010/0035183 A1 | 2/2010 | Nguyen et al. |

FOREIGN PATENT DOCUMENTS

| | | |
|---|---|---|
| EP | 1 582 346 A2 | 10/2005 |
| EP | 1582346 A2 | 10/2005 |
| EP | 1627732 A1 | 2/2006 |
| EP | 1 728 838 A1 | 12/2006 |
| EP | 1 759 836 A2 | 3/2007 |
| JP | 2003248285 * | 9/2003 |
| JP | 2006-335988 | 12/2006 |
| WO | WO 96/18133 A1 | 6/1996 |
| WO | WO 01/09682 A2 | 2/2001 |
| WO | WO 2004/081662 A2 | 9/2004 |
| WO | WO 2004/101280 A1 | 11/2004 |

\* cited by examiner

MATERIALS FOR LITHOGRAPHIC PLATES COATINGS, LITHOGRAPHIC PLATES AND COATINGS CONTAINING SAME, METHODS OF PREPARATION AND USE

CROSS REFERENCE TO RELATED APPLICATIONS

This application claims priority on U.S. provisional application No. 60/747,474, filed on May 17, 2006, which is herein incorporated by reference.

FIELD OF THE INVENTION

This invention relates to novel materials useful for lithographic plates coatings and to plates, coatings and coating solutions containing these materials. More specifically, these new materials and coating solutions are useful in the preparation of coating for lithographic offset printing plates for direct digital imaging by near-infrared laser radiation.

BACKGROUND OF THE INVENTION

On-press developable negative-working lithographic offset printing plates are known in the prior art. Fox example, U.S. Pat. No. 5,569,573 teaches lithographic printing plates comprising a laser imaging layer containing microencapsulated oleophilic materials in hydrophilic polymer binders. EP 0 770 495 A1 teaches lithographic printing plates comprising near infrared absorption materials, polymer binders and thermoplastic particles capable of coalescing under heat. U.S. Pat. No. 6,983,694 teach on-press developable negative-working offset printing plates coated with near infrared sensitive coating compositions comprising thermoplastic polymer particles, such as polystyrene or poly(acrylonitrile-co-styrene) particles, non-reactive hydrophilic polymer binder and near infrared absorption dyes.

Also, U.S. Pat. No. 6,261,740 teaches negative-working offset printing plates coated with near infrared sensitive coating compositions containing methoxymethacrylamide copolymers, phenolic resins, iodonium salts and near infrared absorption dyes. U.S. Pat. Nos. 6,124,425 and 6,177,182 teach on-press developable negative-working offset printing plates coated with thermally near-infrared absorbing polymers, which undergo cross -linking reactions via cationic polymerization upon exposure to near infrared radiation. The near infrared chromophoric moieties are functionalized to the polymeric backbone via ether and ammonium bonds. U.S. Pat. No. 6,960,422 teaches negative-working offset printing plates, which contain a near infrared sensitive base-coat compositions comprising molecular near infrared dyes, radical generators, radical polymerizable urethane compounds, reactive polymer binders and other additives.

Moreover, U.S. Pat. No. 6,969,575 and 7,001,704 teach on-press developable negative-working offset printing plates having an image-forming layer, which comprise near infrared absorbing microcapsules and acid generator compound. U.S. Pat. Nos. 6,582,882, 6,846,614 and 6,899,994 and co-pending US patent applications Ser. No. 2005/0123853 teach on-press developable negative-working offset printing plates, which are coated with thermally imageable compositions containing polymer binders, initiator systems and polymerizable components. The described polymer binders are copolymers having non-reactive polyethylene oxide and polypropylene block, or graft copolymers having non-reactive polyethylene oxide side chains co-polymerized with acrylonitrile, styrene and other monomers. The polymerizable components are viscous liquid oligomers containing multiple acrylic functional groups. The initiator system contains near infrared absorption dyes and radical producing compounds, such as triazine and iodonium salts.

All of these coating compositions and printing plates show some disadvantages such as having a tacky surface which causes difficulties for handling and storage, exhibiting phase separation and/or surface crystallization, being difficult to prepare, requiring high laser power to achieve imaging, having poor substrate adhesion and consequently failing to provide sufficient run length on press, not being developable on-press, exhibiting poor scratching resistance, requiring an over-coating layer and/or a special substrate surface treatment and being expensive to manufacture.

There thus remains a need for new materials and new coatings for lithographic plates that would overcome some or all of the drawbacks of the prior art.

SUMMARY OF THE INVENTION

This invention relates to iodonium salts, acetal copolymers and polymer binders, each comprising at least one functional group capable of undergoing cationic or radical polymerization This invention further relates to the method for preparing the iodonium salts, acetal copolymers and polymer binders of the invention. More specifically, one such method for preparing an iodonium salt of the invention comprises attaching a pendant group to an iodonium salt, wherein the pendant group is obtained by reacting a mono-isocyanate, a di-isocyanate or a poly-isocyanate with an amine or an alcohol, which is terminated by one or more groups each independently selected from acrylate, methacrylate and vinyl-ether.

The present invention further relates to the use of the iodonium salts, acetal copolymers and polymer binders of the invention or a mixture thereof in the preparation of coating solutions and to the coatings produced using these solutions.

The invention also relates to coating solutions and to negative working lithographic printing plate comprising the coatings and/or the iodonium salts, acetal copolymers and polymer binders of the invention.

Thermally Reactive Iodonium salts

The present invention relates to iodonium salt comprising a positively charged iodine atom to which two aryl rings are attached, and a negatively charged counter ion. When exposed to near infrared radiation or heat, these salts are radical and acid generators.

The iodonium salts of the present invention comprise one or more functional groups that can undergo radical and/or cationic polymerization. Upon exposure to heat, the iodonium salt will generate radicals and acid, which will initiate the radical or cationic polymerization of these functional groups. This will contribute to the formation of a network within the irradiated area of the coating.

More specifically, the iodonium salts of the invention may contain radical polymerizable groups, such as acrylate, methacrylate and vinyl ether. These radical polymerizable groups may be pendanted to the aryl rings of the salt via urethane and/or urea bonds. These salts may have the following general structures:

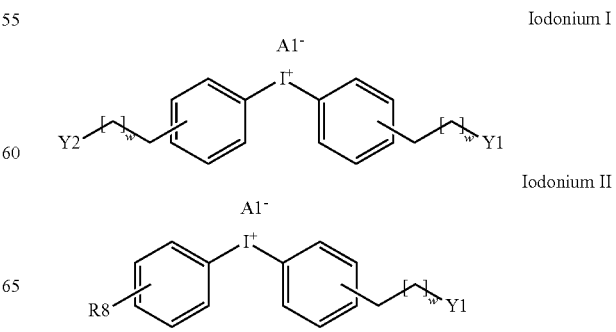

Iodonium I

Iodonium II

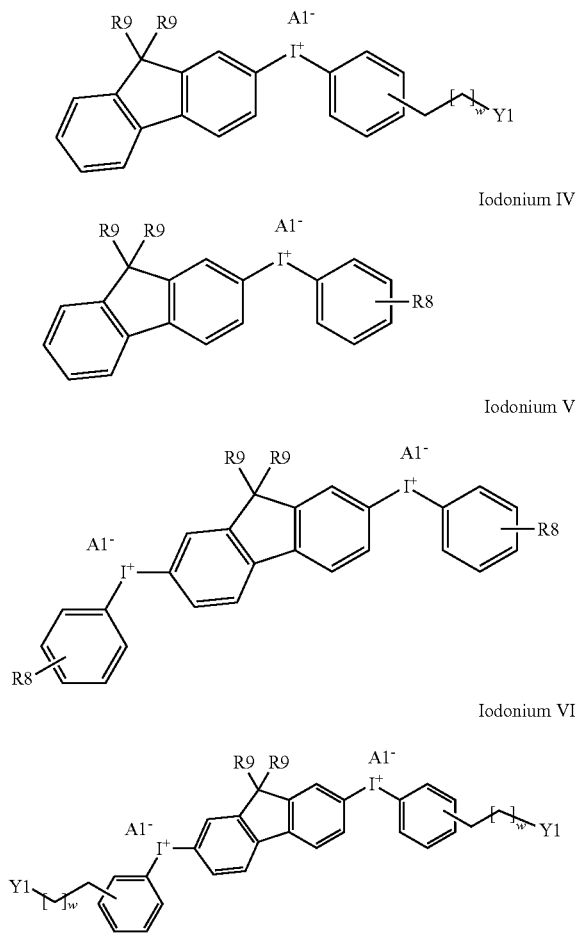

Iodonium III

Iodonium IV

Iodonium V

Iodonium VI wherein:
A1 represents an anionic counter ion selected from tosylate, triflate, hexafluoroantimonate, tetrafluoroborate, tetraphenylborate and triphenyl-n-alkylborate;
w represents the number of repeat unit and may vary between 0 and 18;
R8 and R9 independently represent hydrogen, linear or branched C1-C18 alkyl, alkyl oxy, poly(ethylene oxide), poly(propylene oxide) and may comprise acrylate, methacrylate and vinyl ether terminated groups (In the case of Iodoniums IV and V, either R8, R9 or both R8 and R9 do comprise such acrylate, methacrylate and vinyl ether terminated groups); and
Y1 and Y2 independently represent urethane and/or urea containing compounds, which comprise single or multiple polymerizable functional groups, such as acrylate, methacrylate or vinyl ether.

In a more specific embodiment, Y1 and/or Y2 may be obtained by reacting a mono-isocyanate, di-isocyanate and/or poly-isocyanate with an amine or an alcohol comprising single or multiple acrylate, methacrylate and/or vinyl-ether terminated groups. These isocyanate compounds may be Desmodur™ N100, Desmodur™ N3300, Desmodur™ CB 75N, Desmodur™ I, Desmodur™ W, Desmodur™ M, Desmodur™ H and Desmodur™ TD 80, which are sold by Bayer Canada.

In a specific embodiment, the alcohol comprises multiple acrylate terminated groups. Such alcohol may be are obtained from Sartomer. This alcohol may be pentaerylthritol triacrylate (Trade-name SR 444) and dipentaerylthritol pentaacrylate (Trade-name SR399).

In another specific embodiment, the alcohol comprises single acrylate and methacrylate compounds and may be obtained from Sigma-Aldrich Canada. The alcohol may be 2-hydroxyethylacrylate, 2-hydroxyethylmethacrylate, 4-hydroxybutylacrylate, 4-hydroxybutylmethacrylate, 6-hydroxyhexylacrylate, 6-hydroxyhexylmethacrylate, poly(ethylene glycol) acrylate, poly(ethylene glycol) methacrylate, poly(propylene glycol) acrylate and poly(propylene glycol) methacrylate.

Y1 and Y2 may have the following chemical structures:

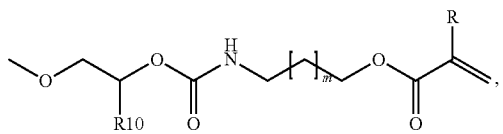

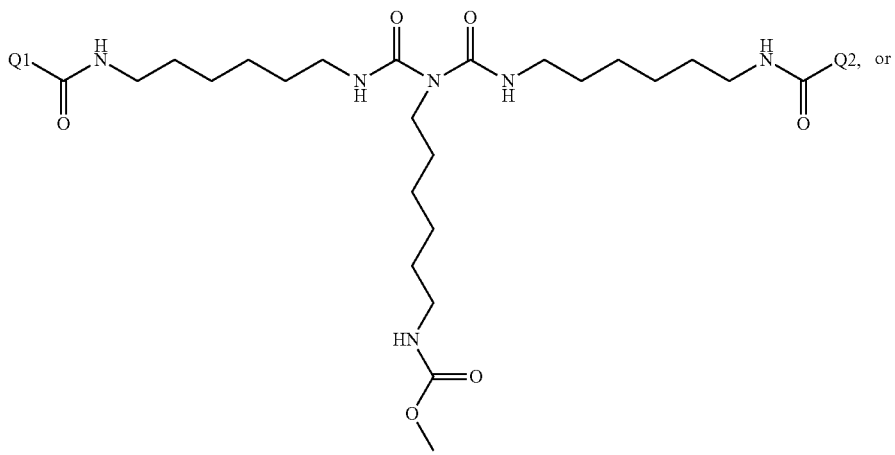

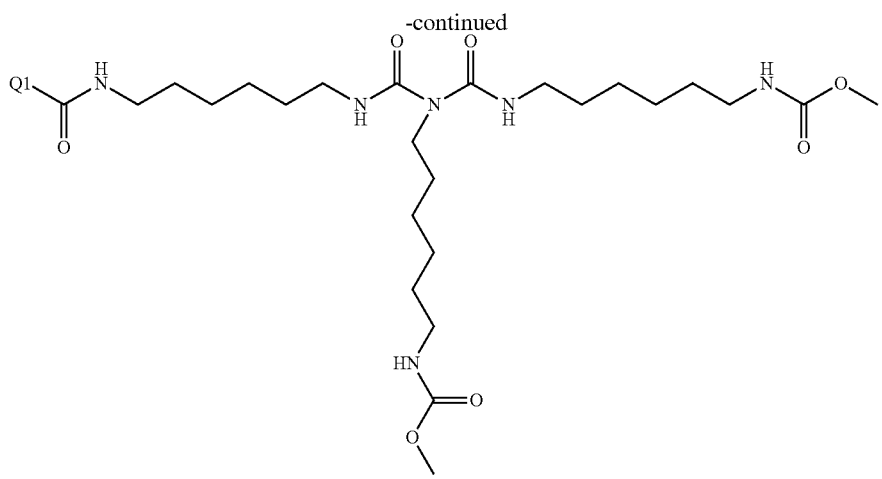

wherein:
  m varies between 1 and 18,
  R is hydrogen or methyl
  R10 is hydrogen or a linear or branched C1-C18 alkyl chain; and
  Q1 and Q2 independently represent an end compound comprising single or multiple polymerizable functional groups.

More specifically, Q1 and Q2 may independently have any of the following structures:

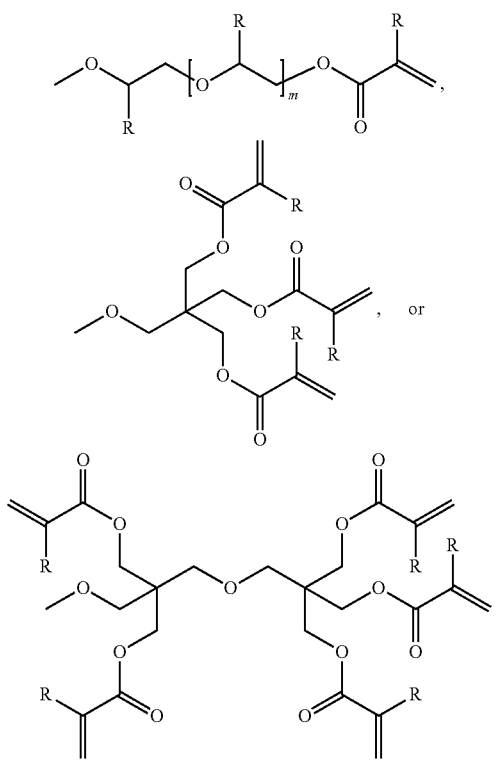

wherein R is hydrogen or methyl.

The synthesis of urethane containing iodonium salts having no reactive (polymerizable) functional groups can be seen in U.S. Pat. No. 6,380,277, which is incorporated herein as reference.

The iodonium salt of the present invention may be used for the preparation of coating solutions and coatings. Such coating may comprise from about 5 to about 60% by solid weight of the iodonium. The coatings are usually prepared by depositing a coating solution comprising the iodonium salt onto a substrate. These solutions comprise a solvent or a mixture of solvent allowing the formation of the coating. Any solvent known to the person of skill in the art to be appropriate for this purpose can be used. Examples of such solvents include n-propanol, water and other similar solvents.

In a specific embodiment, the coating/coating solution of the present invention comprises a mixture of iodonium salts, which may ease the manufacturing process.

Near Infrared Absorbing Dyes

The coating/coating solution of the present invention may also comprise a near infrared absorbing dye which produces heat upon exposure to near infrared radiation. More specifically, this near infrared absorbing dye may be a molecular dye, a dimeric dye, a dendrimeric dye or a polymeric dye. In a specific embodiment, this dye is an acetal copolymer.

This molecular dye, and more particularly this acetal copolymer, may have attached thereto a functional group capable of undergoing cationic or radical polymerization. Therefore, when the iodonium salt produces acid/radicals, this functional group will react with other such functional groups present in the coating, for example that of the iodonium salt, to produce a chemical link, and contribute to the formation of a network within the irradiated area of the coating.

More specifically, the near infrared absorbing acetal copolymers may have a molecular weight greater than about 2,000 g/mol and may either be soluble in organic solvents or in aqueous solutions. Furthermore, they may have the following general structure:

Formula 1

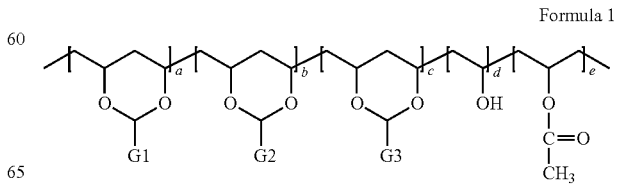

wherein:

G1 represents an optional processing segment that provides solubility in organic solvents such as alcohol, ketone, and ester;

G2 represents an optional thermal reactive segment;

G3 represents a radiation-absorbing segment that exhibits one or more strong absorption bands between 700 and 1100 nm. Optionally, this segment may also exhibit strong absorption bands between 400 and 700 nm;

a, b, c, d and e are molar ratios that can vary from 0.01 to 0.99; and

More specifically, the G1 processing segment of this invention may be a linear or branched alkyl or aryl compound containing cyano, hydroxy, dialkylamino, trialkylammonium salts, ethylene oxide, propylene oxide, methylbenzylsufonyl-carbamate or carboxylic acid and phosphoric acid functional groups.

The G2 thermal reactive segment of this invention may be a linear or branched alkyl or aryl compound and may contain a functional group capable of undergoing radical and/or cationic polymerization, such as acrylate, methacrylate, and vinyl ether.

The G2 thermal reactive segment may have the following structures:

Formula 2

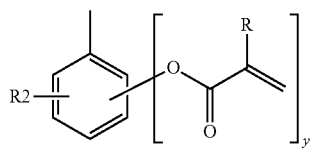

Formula 3

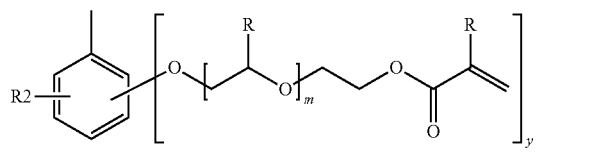

Formula 4

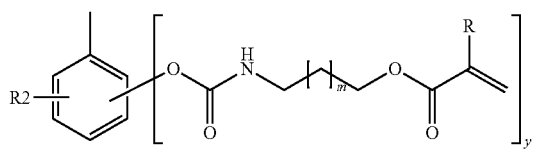

Formula 5

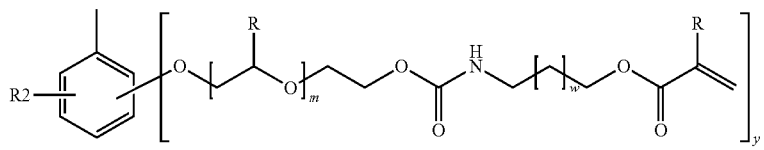

Formula 6

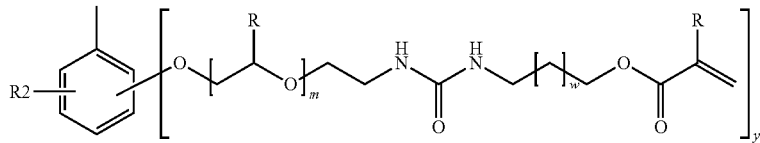

Formula 7

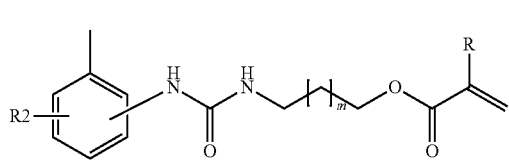

when the optional G1 and/or G2 segments are not present,

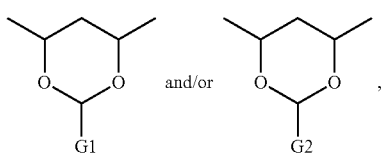

respectively are replaced by

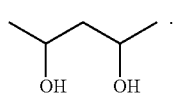

wherein:

R is hydrogen or methyl;

R2 is C1 C8 alkyl or alkoxy;

m and w represent the number of repeat and may vary between 0 and 50;

y is 1 or 2.

In another specific embodiment, the G2 segments may have pendant groups to those illustrated in formulas 2 to 7, but terminated with vinyl ether, alkoxy-methyl acrylamide or alkoxy methacrylamide functional groups.

The G3 segment may be similar to that described in US Patent Publication No. US 2006-0275698 A1, which is incorporated herein as reference. More specifically, the G3 segment may have the following structures:

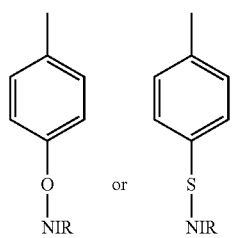

wherein NIR is a near-infrared absorbing chromophore that exhibits one or more strong absorption peaks between 700 and 1100 nm and may optionally exhibit one or more strong absorption peaks between 400 and 700 nm.

The acetal polymer of the invention may also comprise different G3 segments comprising different near-infrared absorbing chromophores.

The near-infrared absorbing chromophores (NIR chromophores) may be near infrared absorbing organic compounds containing cyanine and/or arylimine functional groups. These chromophores may have the following structures:

NIR Chromophore I

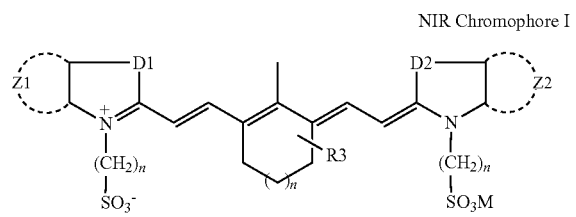

NIR Chromophore II

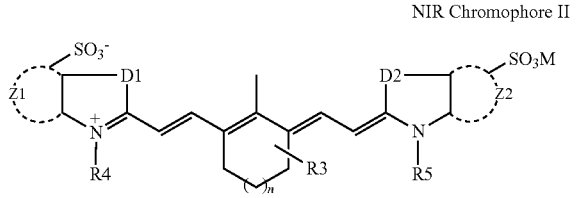

NIR Chromophore III

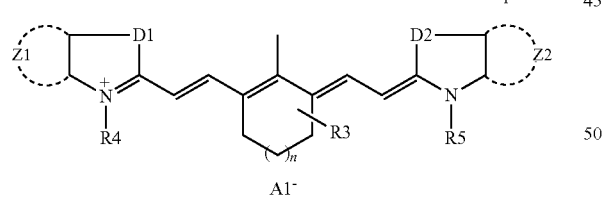

NIR Chromophore IV

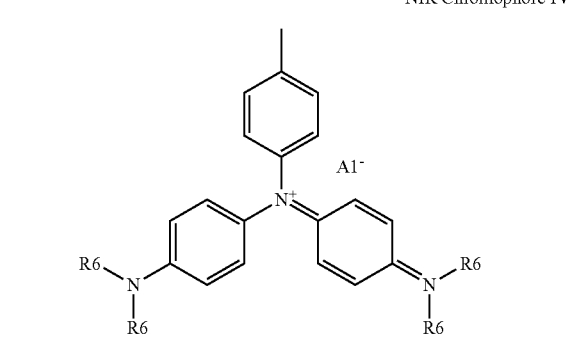

NIR Chromophore V

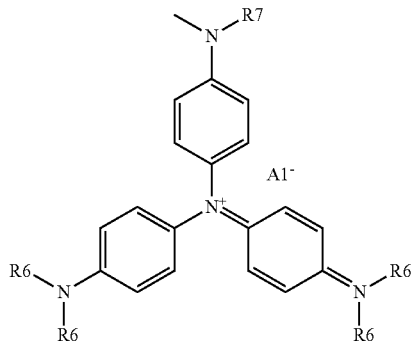

wherein:
D1 and D2 are identical or different and represent —O—, —S—, —Se—, —CH═CH—, and —C(CH3)$_2$;
Z1 and Z2 are identical or different and represent one or more fused substituted or unsubstituted aromatic rings, such as phenyl and naphthyl;
h represents integer number from 2 to 8;
n represents 0 or 1;
M represents hydrogen or a cationic counter ion selected from Na, K, and tetraalkylammonium salts.
A1 represents an anionic counter ion selected from bromide, chloride, iodide, tosylate, triflate, trifluoromethane carbonate, dodecyl benzosylfonate and tetrafluoroborate, tetraphenylborate and triphenyl-n-butylborate.
R3 and R7 represent hydrogen or alkyl; and
R4, R5 and R6 are identical or different and represent alkyl, aryl alkyl, hydroxy alkyl, amino alkyl, carboxy alkyl, sulfo alkyl.

In a specific embodiment, R4, R5 and R6 may represent a polymerizable substituents having the following structure:

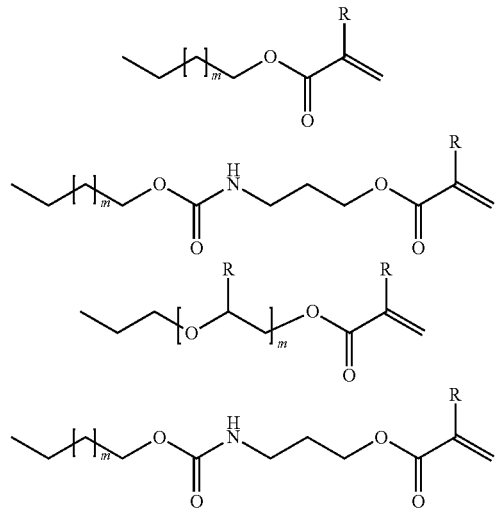

wherein:
m is a number of —CH$_2$— on the alkyl chain and may vary between 0 and 50; and
R is hydrogen or methyl.

The near infrared absorbing acetal copolymers may be used in the coating of the present invention in quantities ranging from about 5 to 50% by solid weight.

Polymer Binders

The coating/coating solution of the present invention may also comprise a polymer binder. This polymer binder may be used in the coating in quantities ranging from about 1 to about 50% by solid weight.

More specifically, the polymer binders of this invention may be polymers, copolymers or dendrimers, which may comprise functional group(s) which can undergo radical and/or cationic polymerization. Therefore, when the iodonium salt produces acid/radicals, these functional groups will react with other such functional groups present in the coating, for example that of the iodonium salt and the dye (if present), to produce chemical links, and contribute to the formation of a network within the coating.

Specifically, these functional groups may be acrylate, methacrylate, and vinyl ether. More specifically, these functional groups may be cation reactive functional groups such as hydroxy, N-methoxymethylacrylamide and N-methoxymethylmethacrylamide.

The polymer binders of the invention may be solvent- and/or water-soluble cellulose ethers comprising a functional group which can undergo radical and/or cationic polymerization. This cellulose ether may be obtained by reacting of 2-isocyanto-ethyl methacrylate with the hydroxymethyl, hydroxyethyl and hydroxypropyl group on the cellulose backbone. The cellulose ether of the invention may have the following structure:

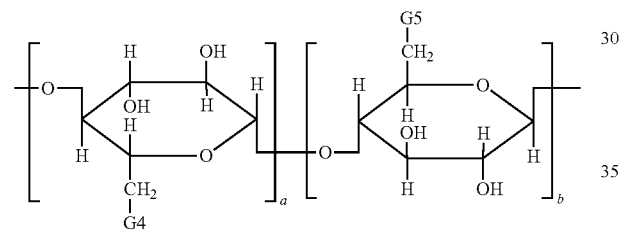

wherein:
G4 is hydroxy, hydroxyethyl and hydroxypropyl.
G5 is the functional group which can undergo radioal and/or cationic polymerization.
More specifically, the G5 groups may have the following structure

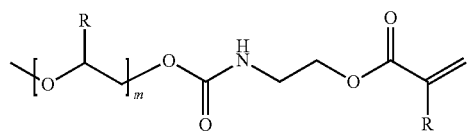

wherein m is 0 or 1 and R is hydrogen or methyl.

The polymer binder of the invention may also be an acetal copolymer which does not absorb near infrared radiation. More precisely, the acetal copolymers of this invention may have the following general structure:

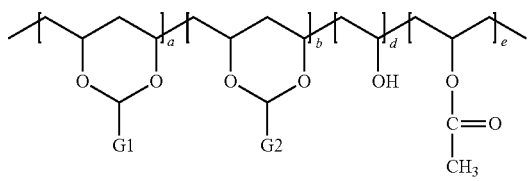

wherein G1, G2, a, b, d and e are similar to those defined in Formula 1 as above and wherein when the optional G1 and/or G2 segments are not present,

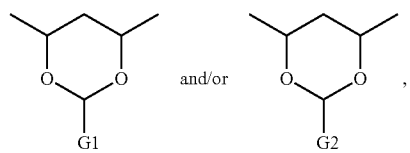

respectively, are replaced by

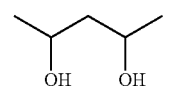

The polymer binders of the invention may also be copolymers comprising a functional group which can undergo radical and/or cationic polymerization. Such copolymers can be obtained from acrylonitrile, styrene, poly(ethylene glycol) acrylate, poly(ethylene glycol) methacrylate and methoxymethylmethacrylamide monomers. More precisely, the copolymers of the invention may be obtained by copolymerizating:

at least one non reactive segment selected from:

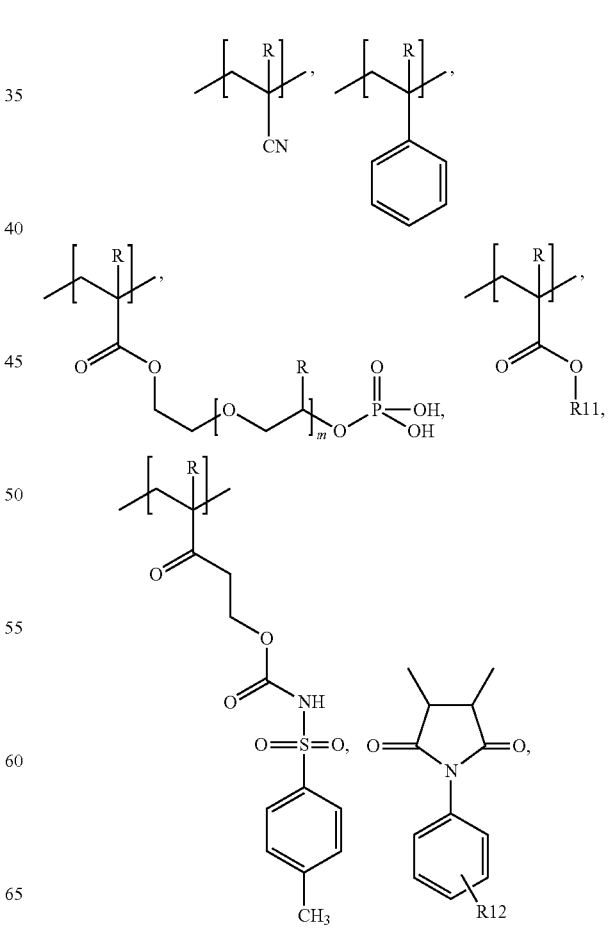

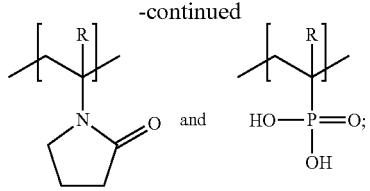

and at least one reactive segment selected from:

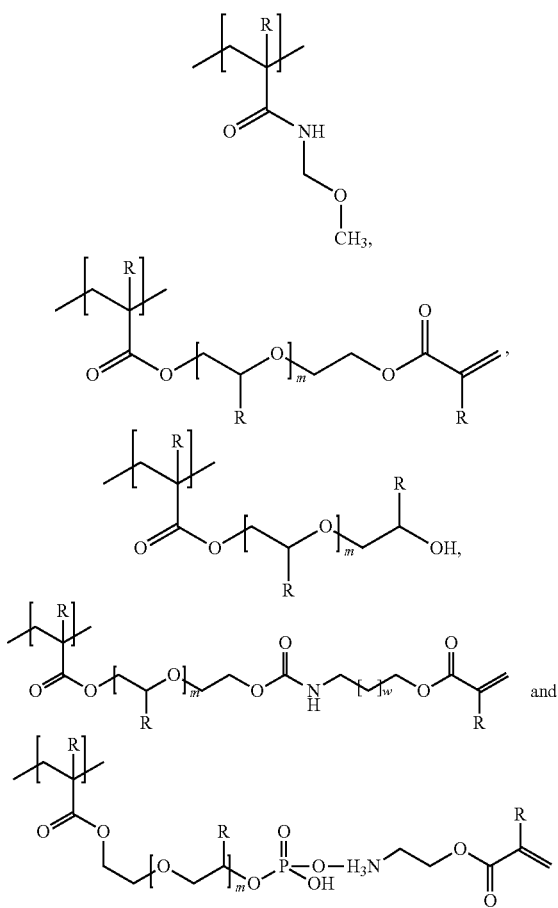

wherein:
- m and w are represent the number of repeat unit and may vary between 0 and 50;
- R is hydrogen or methyl;
- R11 is linear and branched alkyl chain; and
- R12 is alkyl, hydroxyl and carboxylic acid.

The acetal copolymer of the present invention may be used in the preparation of a coating/coating solution. The coating/coating solution may also comprise the iodonium salt of the present invention and a polymer binder in the above mentioned quantities.

The polymer binder of the present invention may be used in the preparation of a coating/coating solution. The coating/coating solution may also comprise the iodonium salt of the present invention and a near-infrared absorbing moiety in the above mentioned quantities.

Colorants and Stabilizers

The coatings/coating solutions of the invention may also comprise colorants to provide good image printout after laser imaging. These colorants of this invention may be the derivatives of triarylpyridine, xanthene and isobenzofuranone. These color-generating compounds may be colorless and then become colored in the presence of free radical or acid. More specifically, these compounds may be:

- 3',6'-bis[N-[2-chlorophenyl]-N-methylamino]spiro[2-butyl-1,1-dioxo[1,2-benz isothiazole-3(3H),9'-(9H)xanthene]](prepared by the method of U.S. Pat. No. 4,345,017);
- 3',6'-bis[N[2-[methanesulfonyl]phenyl]-N-methylamino]spiro[2-butyl-1,1-dioxo[1,2-benzisothiazole-3(3H),9'-(9H)xanthene]](prepared by the method of U.S. Pat. No. 4,345,017);
- 9-Diethylamino[spiro[12H-benzo(a)xanthene-12,1'(3'H)-isobenzofuran)-3'-one] (available from BF Goodrich, Canada);
- 2'-di(phenylmethyl)amino-6'-[diethylamino]spiro[isobenzofuran-1(3H),9'-(9H) -xanthen]-3-one (available from BF Goodrich, Canada);
- 3-[butyl-2-methylindol-3-yl]-3-[1-octyl-2-methylindol-3-yl]-1-(3H) -isobenzo furanone (available from BF Goodrich, Canada);
- 6-[dimethylamino]-3,3-bis[4-dimethylamino]-phenyl-(3H)-isobenzofuranone (available from BF Goodrich, Canada);
- 2-[2-Octyloxyphenyl]4-[4-dimethylaminophenyl]-6-phenylpyridine (available from BF Goodrich, Canada); or
- Leuco lactone dyes, such as Blue-63, GN-169 and Red-40 (available from Yamamoto Chemicals Inc., Japan).

The colorants may be used in the coatings of the present invention in quantities ranging from 0.5 to 5% by solid weight.

The coatings/coating solutions of the invention may also comprise stabilizers to prolong the shelf-life of the printing plates during storage. These stabilizers may be methoxyphenol, hydroxyphenol, phenothiazine, 3-mercapto triazol or monomethyl ether hydroquinone. These stabilizers may be used in the coatings of the present invention in quantities ranging from 0.5 to 5% by solid weight.

Negative-working Lithographic Printing Plates

The coating solutions of the present invention may be used in the preparation of negative-working lithographic printing plates.

This invention therefore also relates to printing plates containing the iodonium salts, the acetal copolymers and/or the polymer binders of the present invention. These lithographic offset printing plates may be directly imaged with near-infrared laser imaging devices in computer-to-plate and digital offset printing technologies.

More specifically, such coating solutions may be used in the production of on-press developable negative-working lithographic offset printing plates that comprise single- or multiple-layer coatings deposited on a substrate such as anodized aluminum, plastic films or paper.

The aluminum substrate may be brushed-grained or electro-grained, then anodized with acidic solutions.

The anodized aluminum substrate may be coated with a polymeric adhesion-promoting layer. The adhesion-promoting and heat insulating layer may be obtained from water solutions containing poly(acrylic acid), poly(acrylic acid-co-vinylphophoric acid) or polyvinyl phosphoric acid, which are then dried using hot air at about 110° C. The coating weight of the adhesion -promoting layer may be between about 0.1 and about 1.0 g/m$^2$.

The thermally reactive coating solutions may be deposited on top of the adhesion-promoting layer and may have a coating weight between about 0.5 and about 2.5 g/m$^2$.

Other embodiments and further scope of applicability of the present invention will become apparent from the detailed description given hereinafter. It should be understood, however, that this detailed description, while indicating preferred embodiments of the invention, is given by way of illustration only, since various changes and modifications within the spirit and scope of the invention will become apparent to those skilled in the art.

BRIEF DESCRIPTION OF THE DRAWINGS

In the appended drawings.

DETAILED DESCRIPTION OF SPECIFIC EMBODIMENTS

Figure 1:
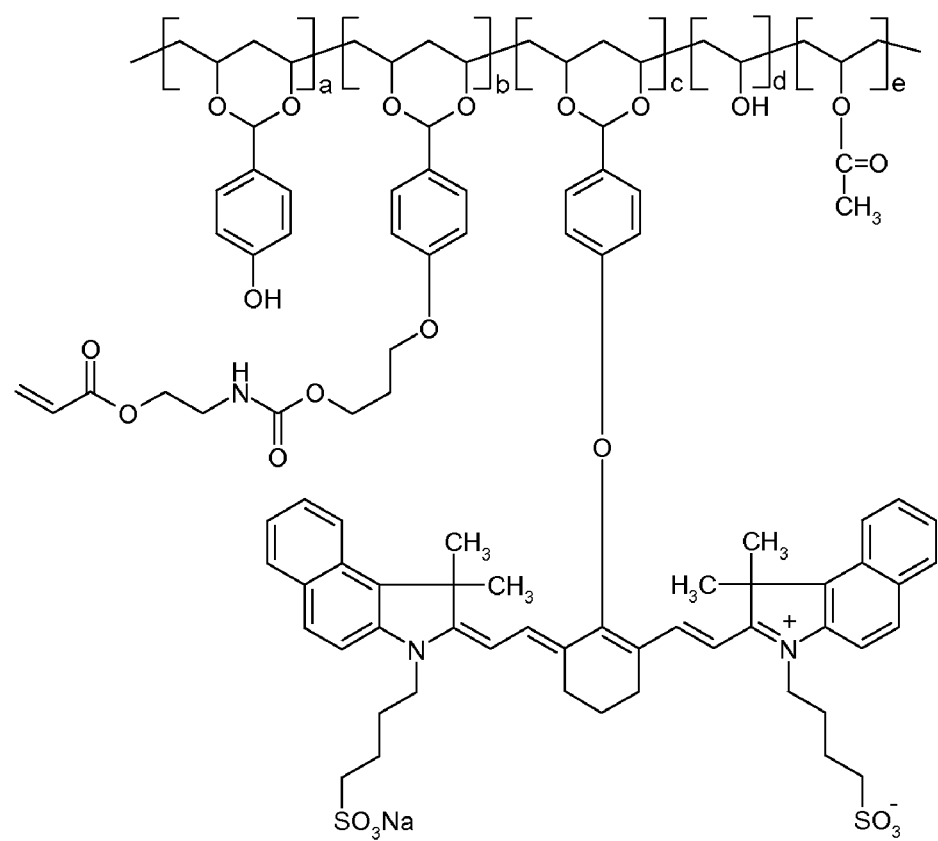
FIG. 1 is the ideal structure of acetal copolymer PVA-01.

The present invention is illustrated in further details by the following non-limiting examples.

In these examples, these syntheses were performed in a 4 necks glass reactor equipped with a water condenser, a mechanical stirrer, a dropping funnel and a nitrogen or air gas inlet. The molecular structures of the obtained materials were determined by proton NMR and FTIR spectroscopy. The average molecular weight of the copolymers obtained was determined by size exclusion chromatography (SEC), using N,N-dimethylformamide (DMF) solutions and calibrated with polystyrene standards. The UV-Visible near-infrared spectra of the synthesized polymers were measured in methanol solutions or on the solid films using a UV-VIS spectrophotometer (PerkinElmer, Model Lambda 35).

Also, the coated plates were imaged using Creo Trendsetter 3244 equipped with 830 nm lasers. The imaged plate was mounted on AB Dick duplicator press using black ink (available from Pacific Inks, Vietnam) and fountain solution containing 3.0 parts of MYLAN-FS100 in 97.0 parts of water (available from MyLan Chemicals Inc., Vietnam).

Synthesis of the Reactive Near-infrared Sensitizing Acetal Copolymers (Dyes):

EXAMPLE 1

The thermally reactive near-infrared sensitizing acetal copolymer PVA-01 was synthesized by adding, by portions, 90 grams of polyvinyl alcohol (Celvol™ 103, a 98% hydrolyzed polyvinyl acetate having an average molecular weight of about 18,000) to a reaction flask containing 500 grams of dimethylsulfoxide (DMSO) at 60° C., under nitrogen atmosphere and with constant stirring. After complete dissolution, 3 ml of concentrated sulfuric acid, which acts as a catalyst for this reaction, were added to the flask. After thirty minutes, 12.2 grams of 4-hydroxybenzaldehyde (100 mmole, available from Sigma-Aldrich, Canada) were slowly added to the flask and the mixture was stirred at 60° C. for 4 hours. Then, 1 gram of sodium hydride (60% in mineral oil, available from Sigma-Aldrich, Canada) was slowly added into the reaction. After hydrogen gas was no longer produced from the reaction, 3.0 grams of 3-bromopropyl-methacryloyl-ethyl carbamate (see structure below, available from American Dye Source Inc., Canada) was added into the reaction mixture.

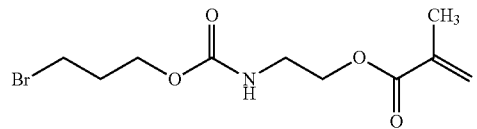

3-bromopropyl-methacryloyl-ethyl carbamate.

The reaction was continued for 30 minutes, then 20 grams of 2-[2-[2-chloro-3-[[1,3-dihydro-1,1-dimethyl-3-(4-sulfonylbutyl)-2H-benzo[e]indol-2-ylideneFethylidene]-1-cyclohexen-1-yl]ethenyl]-1,1-dimethyl-3-(4-sulfonylbutyl) -1H-benzo[e]indolium hydroxy inner salt, sodium salt (13mmole, available from American Dye Source, Inc.) was slowly added to the flask. The resulting mixture was stirred at 60° C. for another 5 hours. The reaction product was precipitated in acetone, filtered and washed copiously with acetone. It was then dried in air until constant weight.

The UV-Vis-NIR spectrum of the obtained PVA-01 thermally reactive near-infrared absorbing acetal copolymer was recorded in methanol and exhibited a strong absorption band at 803 nm. The ideal structure of the PVA-01 near-infrared absorbing acetal copolymer is shown in FIG. 1, wherein a=6.65%, b=1.00%, c=2.35%, d=88.00% and e=2.00%.

EXAMPLE 2

The thermally reactive near-infrared absorbing acetal copolymer PVA-01 was synthesized by adding, by portions, 90 grams of polyvinyl alcohol (Celvol™ 103, a 98% hydrolyzed polyvinyl acetate having an average molecular weight of about 18,000) to a reaction flask containing 500 grams of dimethylsulfoxide (DMSO) at 60° C., under nitrogen atmosphere and with constant stirring. After complete dissolution, 3 ml of concentrated sulfuric acid, which acts as a catalyst for this reaction, were added to the flask. After thirty minutes, 12.2 grams of 4-hydroxybenzaldehyde (100 mmole, available from Sigma-Aldrich, Canada) were slowly added to the flask and the mixture was stirred at 60° C. for 4 hours. Then, 1 gram of sodium hydride (60% in mineral oil, available from Sigma-Aldrich, Canada) was slowly added into the reaction. After hydrogen gas was no longer produced from the reaction, 3.0 grams of 3-bromopropyl-methacryloyl-ethyl carbamate was added into the reaction mixture. The reaction was continued for 30 minutes, then 20 grams of 2-[2-[2-chloro-3-[2-(1,3-dihydro-1,3,3-trimethyl-2H-indol -2-ylidene)-ethylidene]-1-cyclohexen-1-yl]ethenyl]-1,3,3-trimethyl-1H-indolium chloride (available from American Dye Source, Inc.) was slowly added to the flask. The resulting mixture was stirred at 60° C. for another 3 hours. Then, 5 grams of sodium tetraphenylborate was added into the reaction flask and it continued to stir for additional 2 hours. The reaction product was precipitated in de-ionized water, filtered and washed copiously with water. It was then dried in air until constant weight.

Figure 2:
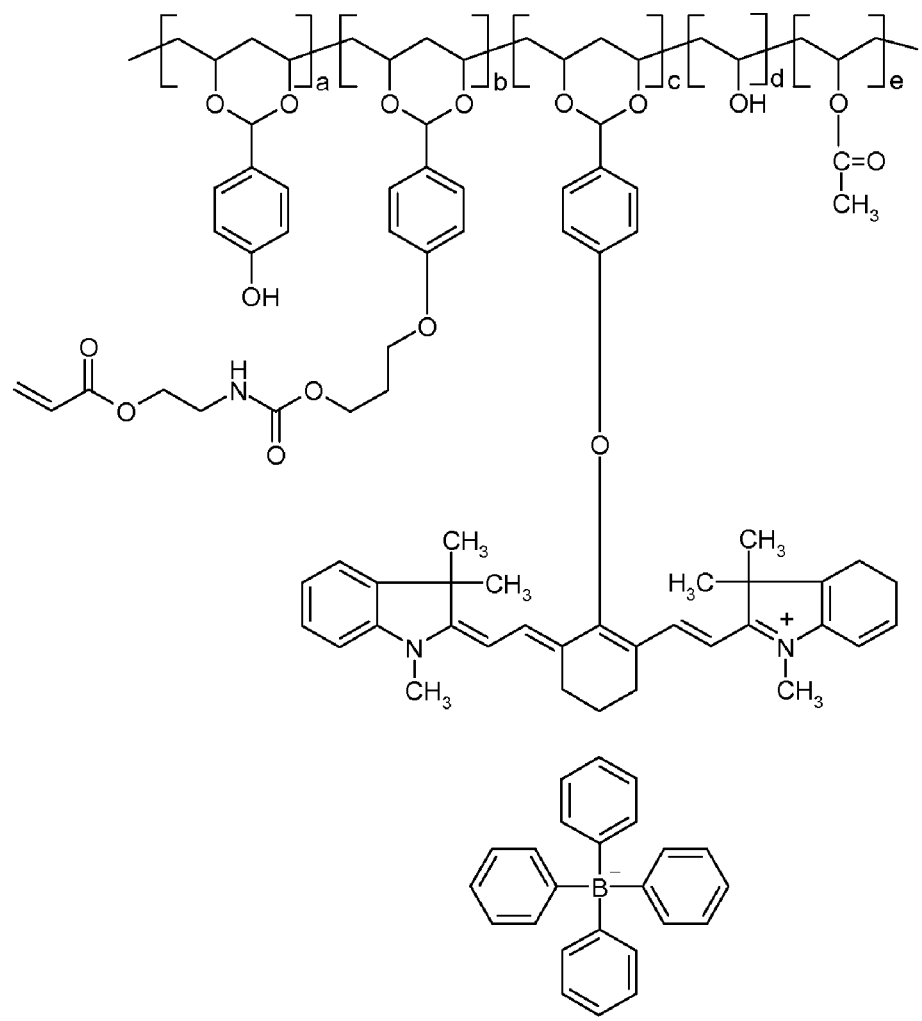
FIG. 2 is the ideal structure of acetal copolymer PVA-02.

The UV-Vis-NIR spectrum of the obtained PVA-02 thermally reactive near-infrared absorbing acetal copolymer was recorded on a thin film and exhibited a strong absorption band at 800 nm. The ideal structure of the PVA-02 near-infrared absorbing acetal copolymer is shown in FIG. 2, wherein a=5.15%, b=1.00%, c=3.85%, d=88.00% and e=2.00%.

EXAMPLE 3

The thermally reactive near-infrared absorbing acetal copolymer, PVA-01, was synthesized by adding, by portions, 90 grams of polyvinyl alcohol (Celvol™ 103, a 98% hydrolyzed polyvinyl acetate having an average molecular weight of about 18,000) to a reaction flask containing 500 grams of dimethylsulfoxide (DMSO) at 60° C., under nitrogen atmosphere and with constant stirring. After complete dissolution, 3 ml of concentrated sulfuric acid, which acts as a catalyst for this reaction, were added to the flask. After thirty minutes, 6.1 grams of 4-hydroxybenzaldehyde (available from Sigma-Aldrich, Canada) were slowly added to the flask and the mixture was stirred at 60° C. for 4 hours. Then, 0.5 grams of sodium hydride (60% in mineral oil, After hydrogen gas was no longer produced from the reaction, 10 grams near infrared absorption containing reactive functional groups having the structure shown below (available from American Dye Source, Inc.) was slowly added to the flask.

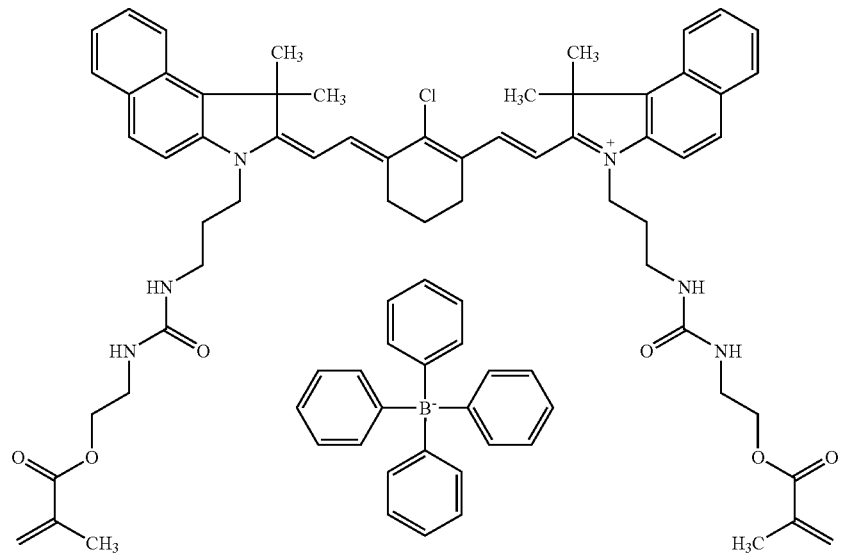

The resulting mixture was stirred at 50° C. for another 5 hours. The reaction product was precipitated in 10 liters of de-ionized water, filtered and washed copiously with water. It was then dried in air until constant weight.

Figure 3:
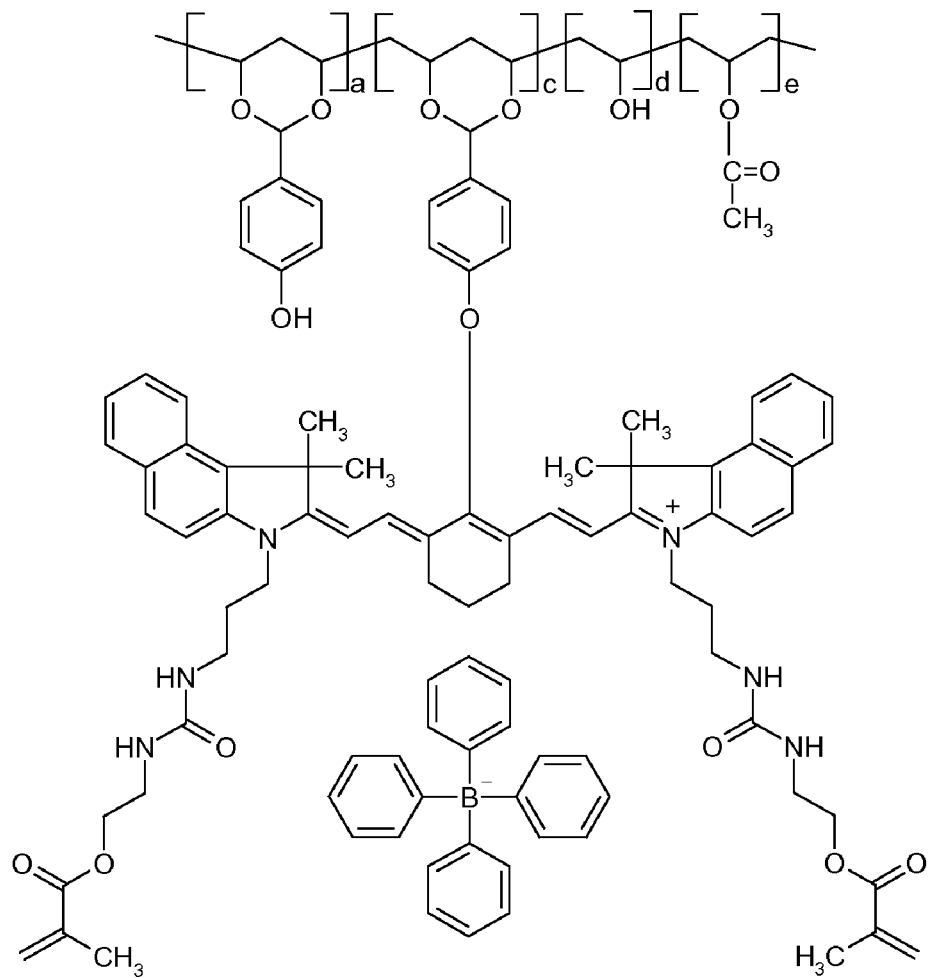
FIG. 3 is the ideal structure of acetal copolymer PVA-03.

The UV-Vis-NIR spectrum of the obtained PVA-03 thermally reactive near-infrared absorbing acetal copolymer was recorded on a thin film and exhibited a strong absorption band at 830 nm. The ideal structure of the near infrared absorbing acetal copolymer PVA-03 is shown in FIG. 3, wherein a=3.42%, c=1.58%, d=93.00% and e=2.00%.

EXAMPLE 4

The thermally reactive near-infrared absorbing acetal copolymer PVA-01 was synthesized by adding, by portions, 90 grams of polyvinyl alcohol (Celvol™ 103, a 98% hydrolyzed polyvinyl acetate having an average molecular weight of about 18,000) to a reaction flask containing 500 grams of dimethylsulfoxide (DMSO) at 60° C., under nitrogen atmosphere and with constant stirring. After complete dissolution, 3 ml of concentrated sulfuric acid, which acts as a catalyst for this reaction, were added to the flask. After thirty minutes, 12.2 grams of 4-hydroxybenzaldehyde (available from Sigma-Aldrich, Canada) were slowly added to the flask and the mixture was stirred at 60° C. for 4 hours. Then, 1 gram of sodium hydride (60% in mineral oil, available from Sigma-Aldrich, Canada) was slowly added into the reaction. When hydrogen gas was no longer produced from the reaction, 11.0 grams of 10 grams of bromo-terminated poly(ethylene glycol) acrylate (see below structure, available from American Dye Source Inc.) was added into the reaction mixture.

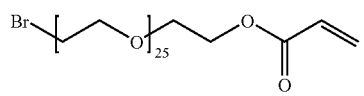

Bromo-terminated poly(ethylene glycol) acrylate

The reaction was continued for 30 minutes, then 20 grams of 2-[2[2-chloro-3-[2-(1,3-dihydro-1,3,3-trimethyl-2H-indol-2-ylidene)-ethylidene]-1-cyclohexen-1-yl]ethenyl]-1,3,3-trimethyl-1H-indolium 4-methylbenzene sulfonate (available from American Dye Source, Inc.) was slowly added to the flask. The resulting mixture was stirred at 60° C. for another 3 hours. Then, 5 grams of sodium tetraphenylborate was added into the reaction flask and it continued to stir for additional 2 hours. The reaction product was precipitated in de-ionized water, filtered and washed copiously with water. It was then dried in air until constant weight.

Figure 4:
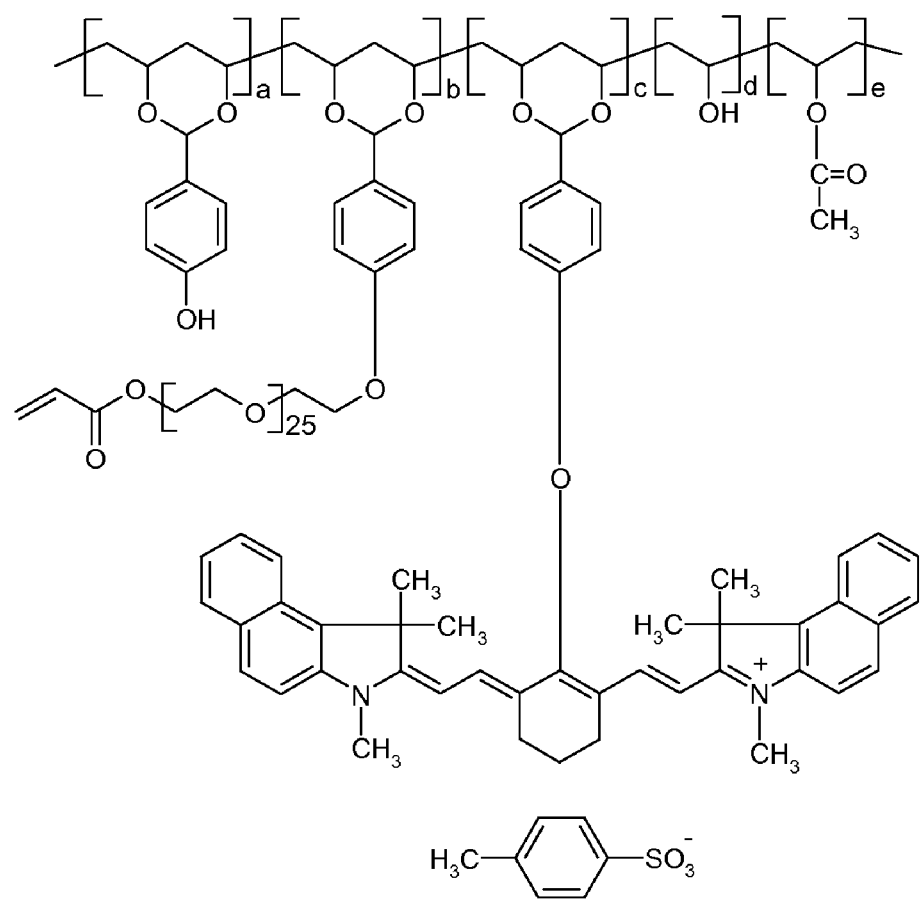
FIG. 4 is the ideal structure of acetal copolymer PVA-04.
Figure 5:
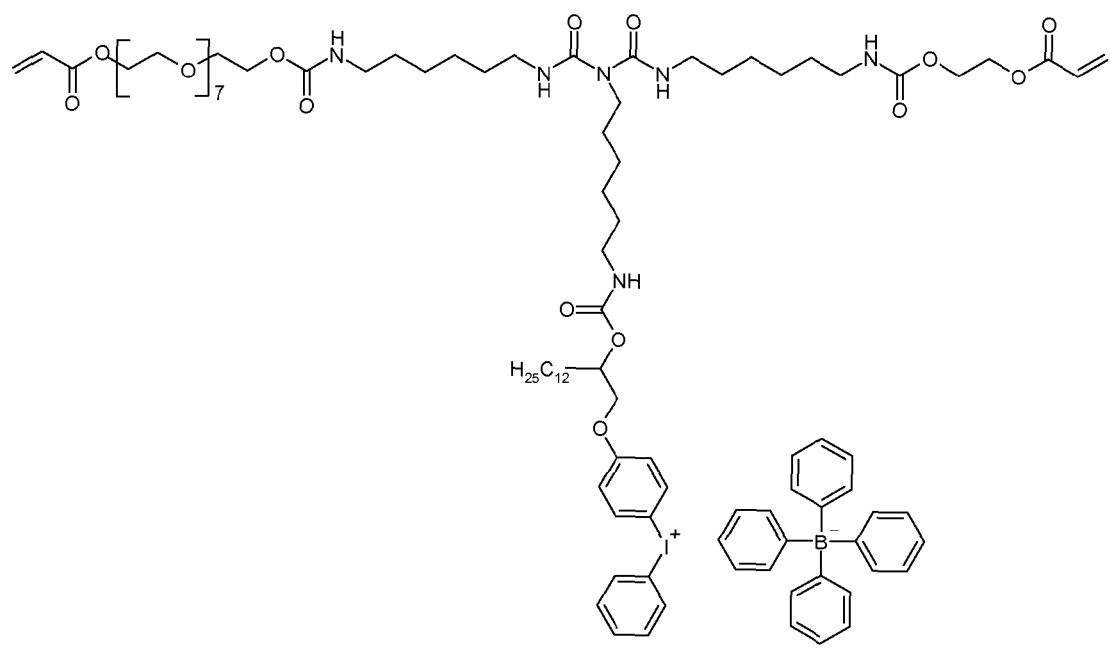
FIG. 5 is the possible structure of a specific embodiment of an iodonium salt of the present invention.

The UV-Vis-NIR spectrum of the obtained PVA-04 thermally reactive near-infrared absorbing acetal copolymer was recorded on a thin film and exhibited a strong absorption band at 800 nm. The ideal structure of the PVA-04 near-infrared absorbing acetal copolymer is shown in FIG. 4, wherein a=5.15%, b=1.00%, c=3.85%, d=88.00% and e=2.00%.

Synthesis of Reactive Iodonium Salts:

For the ease of manufacturing and cost effectiveness, the iodonium salts containing reactive functional groups may be synthesized and used as a mixture of various salts. Further, this mixture may be used directly without further purification.

EXAMPLE 5

A mixture of reactive iodonium tetraphenylborate having possible structures as in FIGS. 5, 6, 7, 8, 9 and 10 was obtained by heating 320 grams of 1,3-dioxolane solution containing 573 grams of Desmodur™ N100 (available from Bayer Canada), 60 grams of 2-hydroxyethylacrylate (available from Sigma-Aldrich, Canada), 245 grams of poly(ethylene glycol) acrylate (Mn ~375, available from Sigma-Aldrich, Canada), 500 grams of pentaerythritol triacrylate (SR-444, available from Sartomer, USA), 1 gram of hydroquinone (available from Sigma-Aldrich, Canada) and 1 gram of dibutyl tin dilaurate (available from Sigma -Aldrich, Canada) to 60° C. under an oxygen atmosphere and constant stirring for 10 hours. A sample of reaction mixture was withdraw from the reaction flask and its FTIR spectrum, recorded on KBr pellet, showed a —N═C═O peak at 2274 cm$^{-1}$. Then, 150 grams of [4-(2-hydroxy-1-tetradecyloxy)phenyl] phenyliodonium tetraphenylborate (available from American Dye Source Inc., Canada) was slowly added into the reaction mixture, which was stirred at 60° C. for an additional 6 hours. The FTIR spectrum then indicated that the —N═C═O peak at 2274 cm−1 had disappeared, which was indicative of the completion of the reaction. The clear viscous product obtained was ready for use.

EXAMPLE 6

Figure 6:
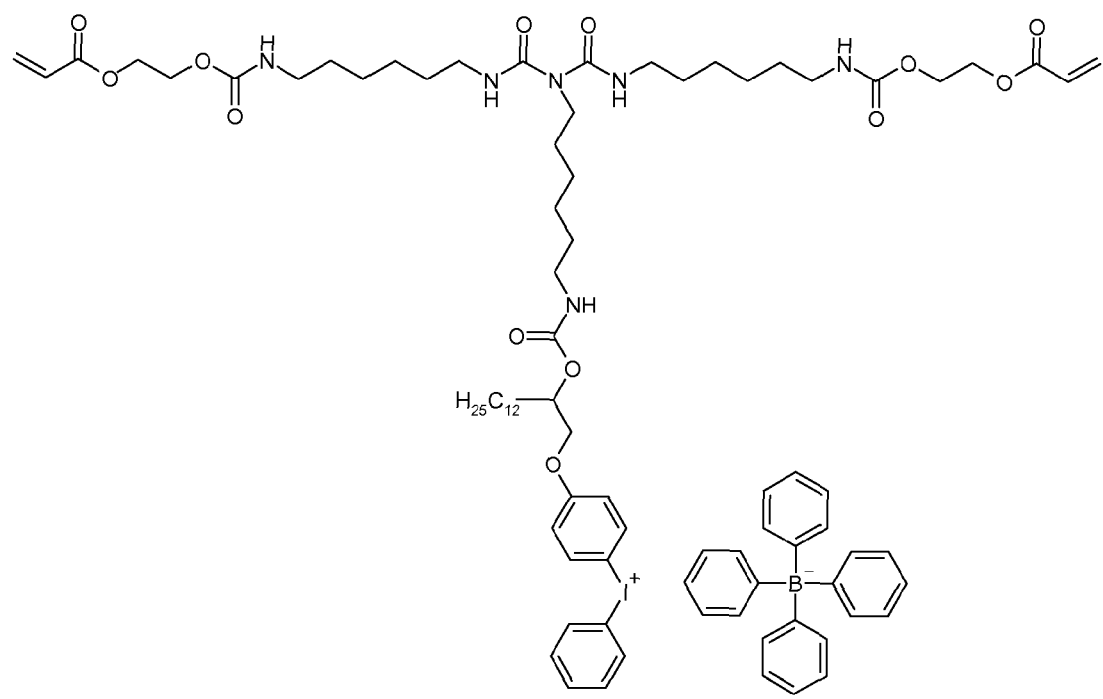
FIG. 6 is the possible structure of a specific embodiment of a n iodonium salt of the present invention.
Figure 7:
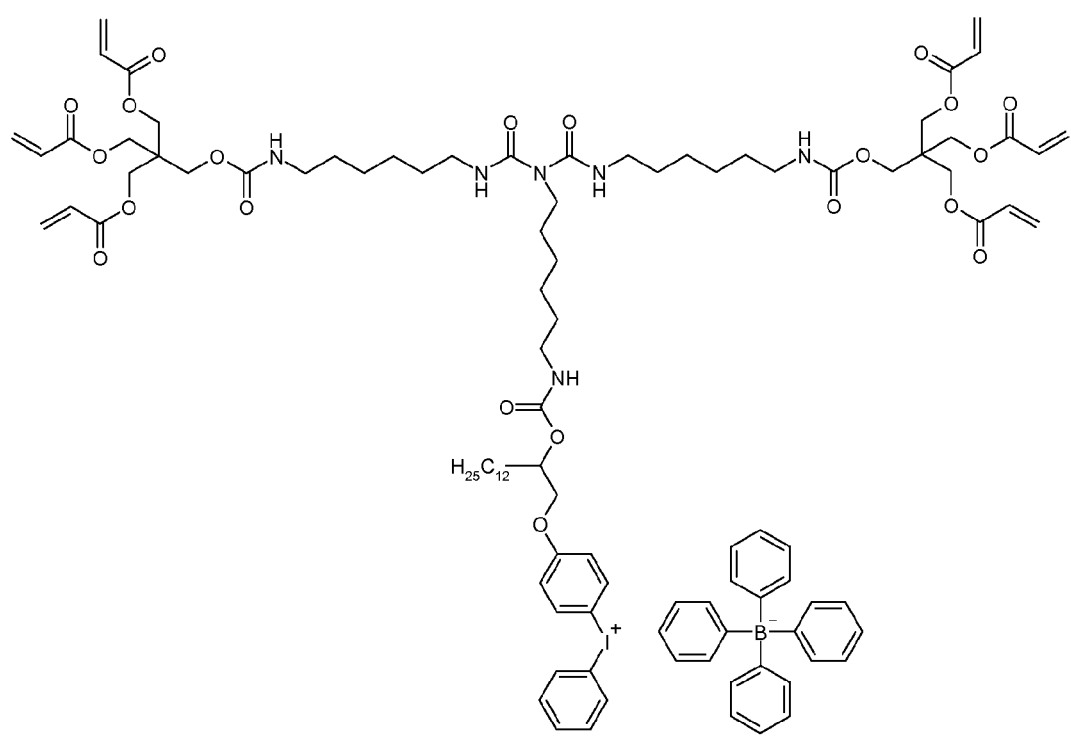
FIG. 7 is the possible structure of a specific embodiment of an iodonium salt of the present invention.
Figure 8:
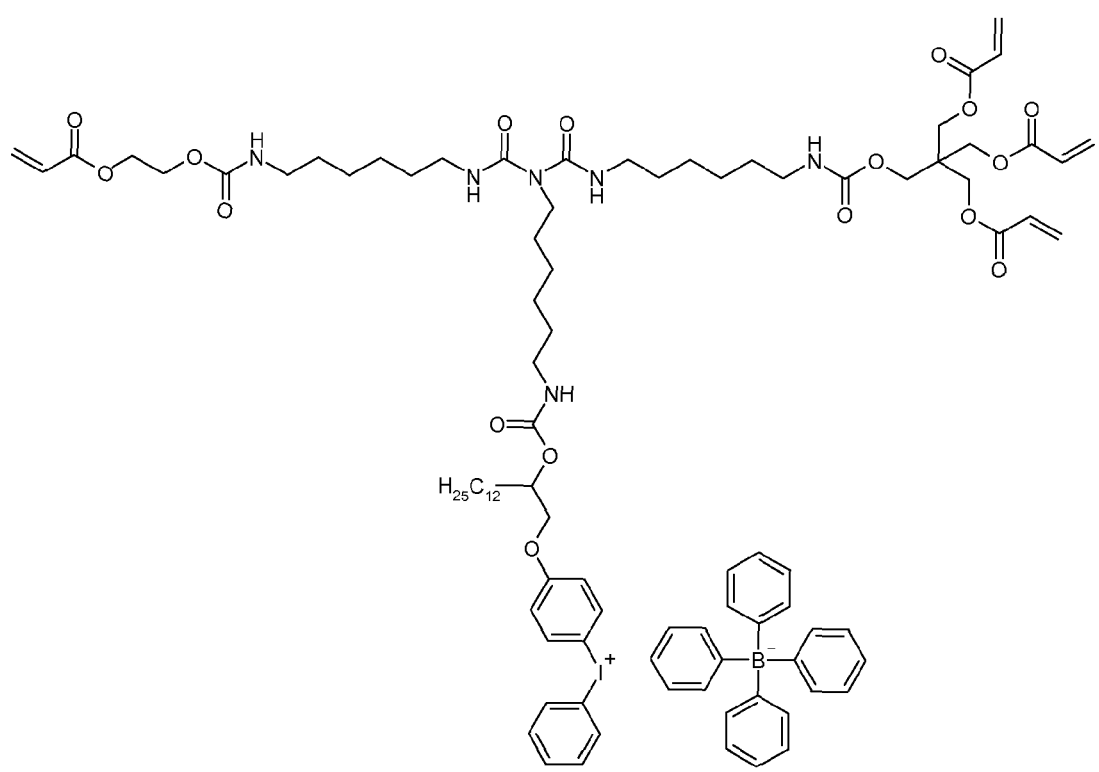
FIG. 8 is the possible structure of a specific embodiment of an iodonium salt of the present invention.

A mixture of reactive iodonium tetraphenylborate having possible structures as in FIGS. 6, 7 and 8) was obtained by heating 320 grams of anhydrous methyl ethyl ketone solution containing 573 grams of Desmodur™ N100 (available from Lanxess, Canada), 138 grams of 2-hydroxyethylacrylate (available from Sigma-Aldrich, Canada), and 500 grams of pentaerythritol triacrylate (SR-444, available from Sartomer, USA), 1 gram of hydroquinone (available from Sigma-Aldrich, Canada) and 1 gram of dibutyl tin dilaurate (available from Sigma-Aldrich, Canada) to 60° C. under an oxygen atmosphere and constant stirring for 10 hours. A sample of reaction mixture was withdraw from the reaction flask and its FTIR spectrum, recorded on KBr pellet, showed a —N═C═O peak at 2274 cm$^{-1}$. Then, 150 grams of [4-(2-hydroxy-1-tetradecyloxy)phenyl] phenyliodonium tetraphenylborate (available from American Dye Source Inc., Canada) was slowly added into the reaction mixture, which was stirred at 60° C. for an additional 6 hours. The FTIR spectrum then indicated that the —N═C═O peak at 2274 cm-1 had disappeared, which was indicative of the completion of the reaction. The clear viscous product obtained was ready for use.

EXAMPLE 7

Figure 9:
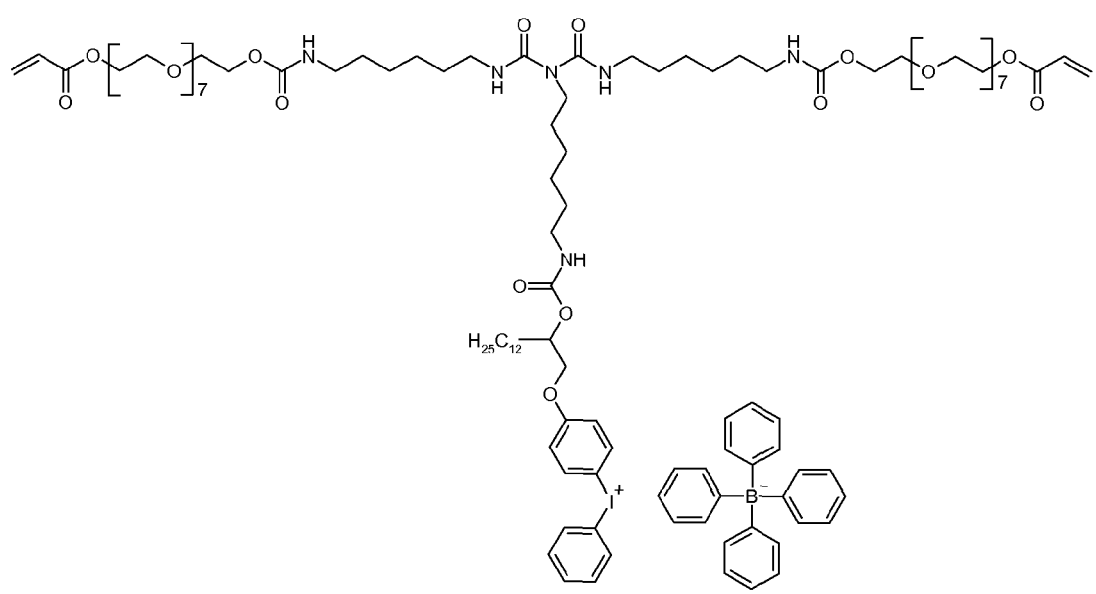
FIG. 9 is the possible structure of a specific embodiment of an iodonium salt of the present invention.
Figure 10:
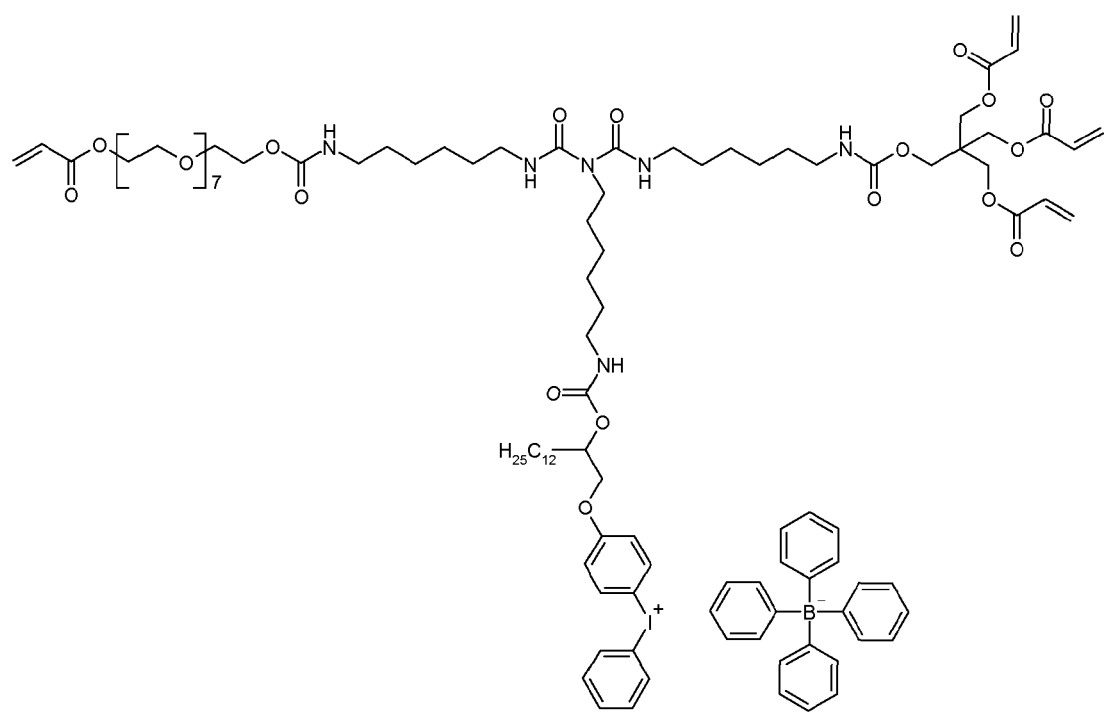
FIG. 10 is the possible structure of a specific embodiment of an iodonium salt of the present invention.
Figure 11:
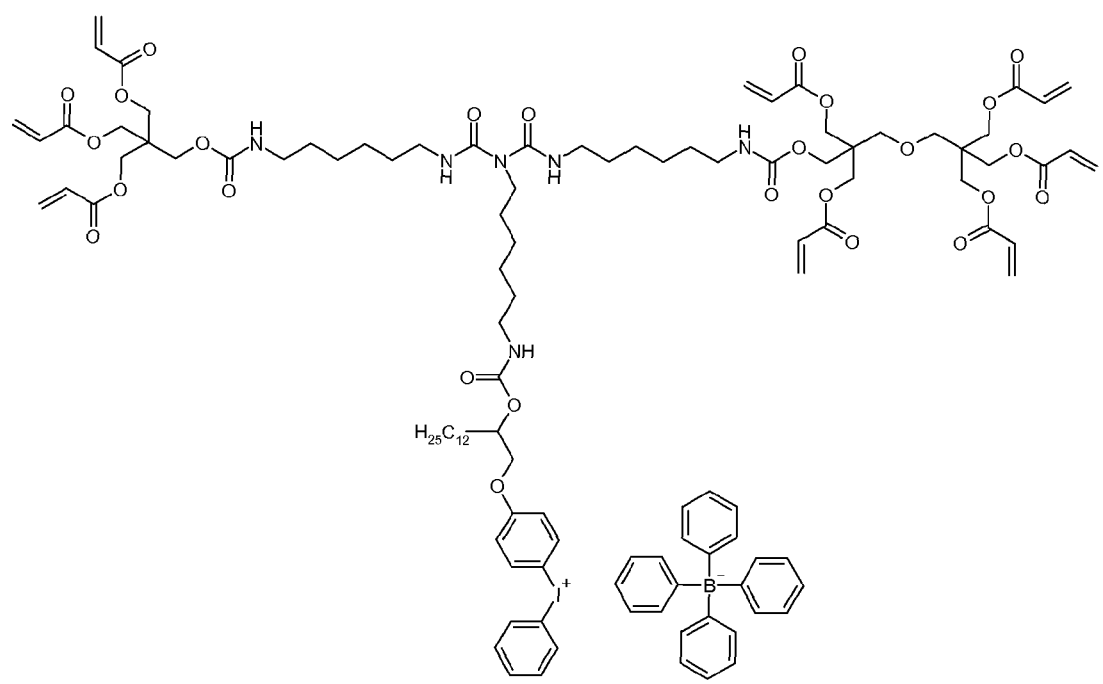
FIG. 11 is the possible structure of a specific embodiment of an iodonium salt of the present invention.
Figure 12:
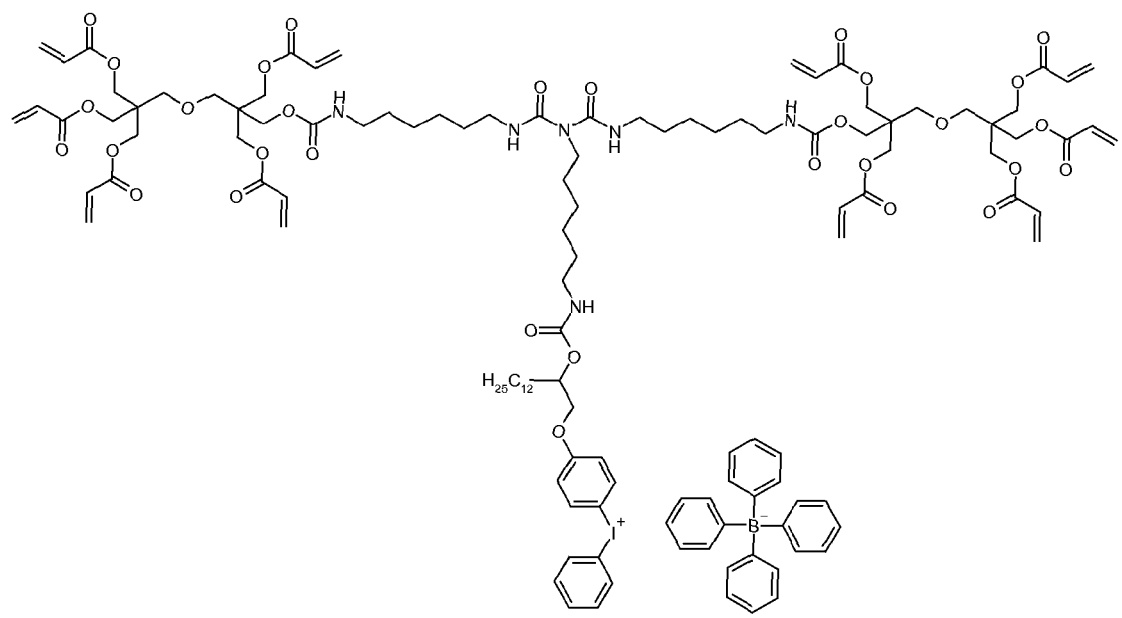
FIG. 12 is the possible structure of a specific embodiment of an iodonium salt of the present invention.
Figure 13:
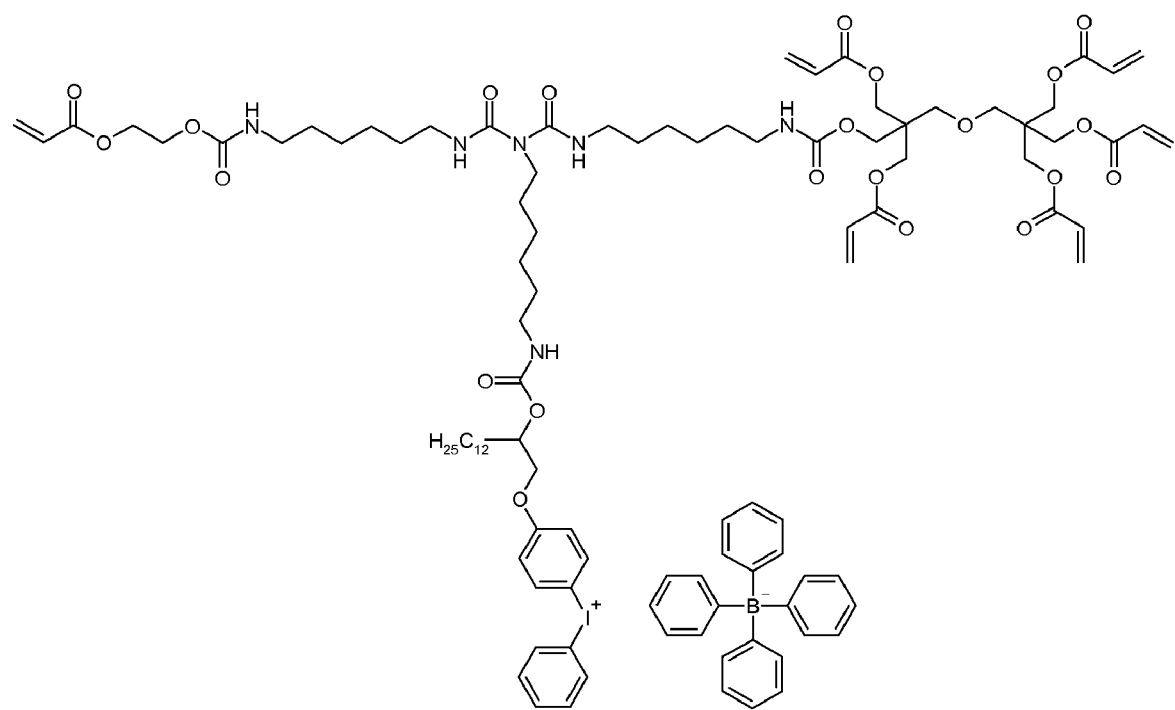
FIG. 13 is the possible structure of a specific embodiment of an iodonium salt of the present invention.

A mixture of reactive iodonium tetraphenylborate having possible structures as in FIGS. 8, 9 and 10 was obtained by heating 320 grams of methyl ethyl ketone solution containing 573 grams of Desmodur™ N100 (available from Lanxess, Canada), 430 grams of poly(ethylene glycol) acrylate (Mn ~375, available from Sigma-Aldrich, Canada), 500 grams of pentaerythritol triacrylate (SR-444, available from Sartomer, USA) and 1 gram of hydroquinone (available from Sigma-Aldrich, Canada) and 1 gram of dibutyl tin dilaurate (available from Sigma-Aldrich, Canada) to 60° C. under oxygen atmosphere and constant stirring for 10 hours. A sample of reaction mixture was withdraw from the reaction flask and its FTIR spectrum, recorded on KBr pellet, showed a —N═C═O peak at 2274 cm$^{-1}$. Then, 150 grams of [4-(2-hydroxy-1-tetradecyloxy)phenyl] phenyliodonium tetraphenylborate (available from American Dye Source Inc., Canada) was slowly added into the reaction mixture, which was stirred at 60° C. for an additional 6 hours. The FTIR spectrum then indicated that the —N═C═O peak at 2274 cm$^{-1}$ had disappeared, which was indicative of the completion of the reaction. The clear viscous product obtained was ready for use.

EXAMPLE 8

A mixture of reactive iodonium tetraphenylborate having possible structures as in FIGS. 6, 7, 11, 12 and 13 was obtained by heating 320 grams of 1,3-dioxolane solution containing 573 grams of Desmodur™ N100 (available from Bayer Canada), 50 grams of 2-hydroxyethylmethacrylate (available from Sigma-Aldrich, Canada), 275 grams of pentaerythritol triacrylate (SR-444, available from Sartomer, USA), 780 grams of dipentaerythritol pentaacrylate (SR-399 available from Sartomer, USA), 1 gram of hydroquinone (available from Sigma-Aldrich, Canada) and 1 gram of dibutyl tin dilaurate (available from Sigma-Aldrich, Canada) to 60° C. under an oxygen atmosphere and constant stirring for 10 hours. A sample of reaction mixture was withdraw from the reaction flask and its FTIR spectrum, recorded on KBr pellet, showed a —N═C═O peak at 2274 cm-1. Then, 150 grams of [4-(2-hydroxy-1-tetradecyloxy)phenyl] phenyliodonium tetraphenylborate (available from American Dye Source Inc., Canada) was slowly added into the reaction mixture, which was stirred at 60° C. for an additional 6 hours. The FTIR spectrum indicated that the —N═C═O peak at 2274 cm-1 had disappeared, which was indicative of the completion of the reaction. The clear viscous product obtained was ready for use.

EXAMPLE 9

A mixture of reactive iodonium tetraphenylborate having possible structures as in FIGS. 7, 9, 10, 11 and 12 was obtained by heating 137 grams of 1,3-dioxolane solution containing 245 grams of Desmodur™ N100 (available from Bayer Canada), 310 grams of poly(ethylene glycol) acrylate (Mn~375, available from Sigma-Aldrich, Canada), 244 grams of pentaerythritol triacrylate (SR-444, available from Sartomer, USA), 100 grams of dipentaerythritol pentaacrylate (SR-399 available from Sartomer, USA), 1 gram of hydroquinone (available from Sigma-Aldrich, Canada) and 1 gram of dibutyl tin dilaurate (available from Sigma-Aldrich, Canada) to 60° C. under an oxygen atmosphere and constant stirring for 10 hours. A sample of reaction mixture was withdraw from the reaction flask and its FTIR spectrum, recorded on KBr pellet, showed a —N=C=O peak at 2274 cm$^{-1}$. Then, 75 grams of [4-(2-hydroxy-1-tetradecyloxy)phenyl] phenyliodonium tetraphenylborate (available from American Dye Source Inc., Canada) was slowly added into the reaction mixture, which was stirred at 60° C. for an additional 6 hours. The FTIR spectrum then indicated that the —N=C=O peak at 2274cm$^{-1}$ had disappeared, which was indicative of the completion of the reaction. The clear viscous product obtained was ready for use.

EXAMPLE 10

Figure 14:
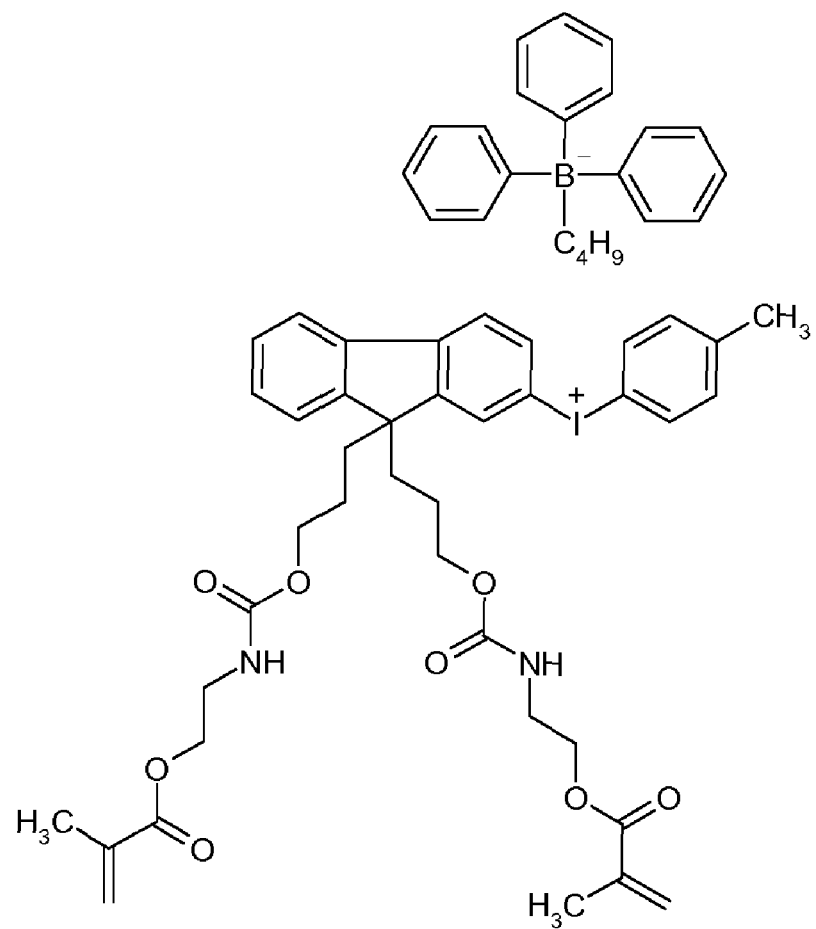
FIG. 14 is the ideal structure of a specific embodiment of an iodonium salt synthesized from fluorene compound;.

Reactive iodonium salt having the structure as shown in Figure 14 was synthesized by slowly adding 31.5 grams of 2-isocyanato-ethylmethacrylate into 300 ml solution of 1,3-dioxolane dissolving with 80 grams of [2-[9,9-(3-hydroxypropyl)fluorenyl] 4-methylphenyliodonium triphenyl-n-butylborate and 0.1 grams of dibutyl tin dilaurate at 60° C. under constant stirring and an oxygen atmosphere. The reaction was monitored by FTIR, which indicated that the reaction was completed within 5 hours. The product was precipitated in de-ionized water, filtered and washed copiously with de-ionized water. It was then washed with ether and dried in air until constant weight.

The iodonium salts of FIGS. 20-25 were also synthesized. Synthesis of Thermally Reactive Polymer Binders:

EXAMPLE 11

Figure 15:
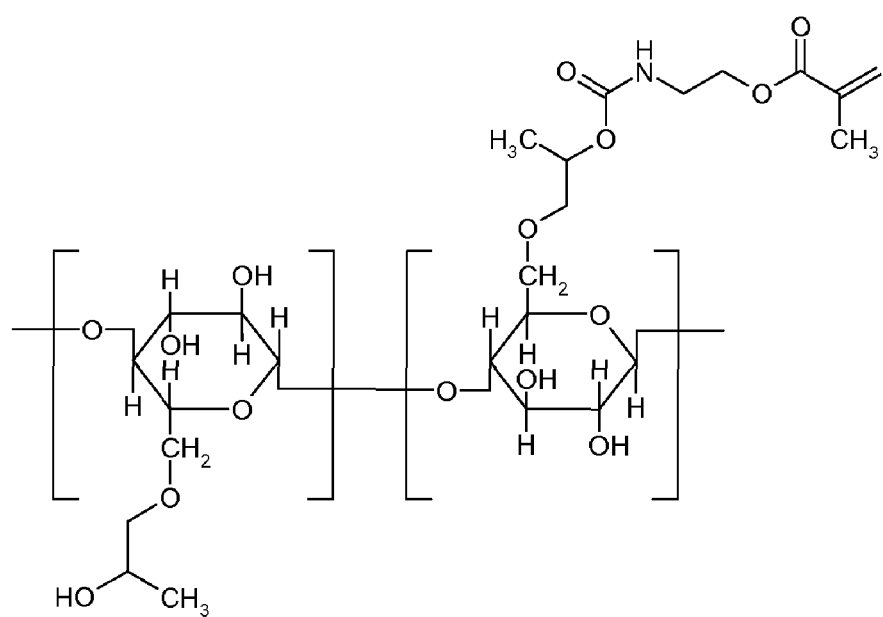
FIG. 15 is the ideal structure of polymer binder RPB-01.

The thermally reactive polymer binder, RPB-01 was synthesized by adding, by portions, 25 grams of hydroxypropyl cellulose (Klucel® E, available from Hercules, USA) to a reaction flask containing 500 grams of 1,3-dioxolane at 60° C., under air atmosphere and with constant stirring. After complete dissolution, 3 drops of dibutyl tin dilaurate, which acts as a catalyst for this reaction, were added to the flask. Then, 5.0 grams of 2-isocyanatoethylmethacrylate (available from American Dye Source, Canada) were slowly added to the reaction flask and the mixture was stirred at 60° C. for 7 hours. FTIR spectrum of the polymer on KBr pellet indicated that the reaction was completed with the disappearance of the—N=C=O peak at 2274cm$^{-1}$. The ideal structure of RPB-01 is shown in FIG. 15. n-Propanol was added into the reaction to provide 5.0% solid content solution.

EXAMPLE 12

The reactive polymer binder, RPB-02 was synthesized in way similar to that of Example 11 with the exception that 10 grams of 2-isocyanatoethylmethacrylate was used in the reaction. The ideal structure of RPB-02 is similar to that of RPB-01 with more reactive functional groups present in the polymer. n-Propanol was added into the reaction to provide 5.0% solid content solution.

EXAMPLE 13

Figure 16:
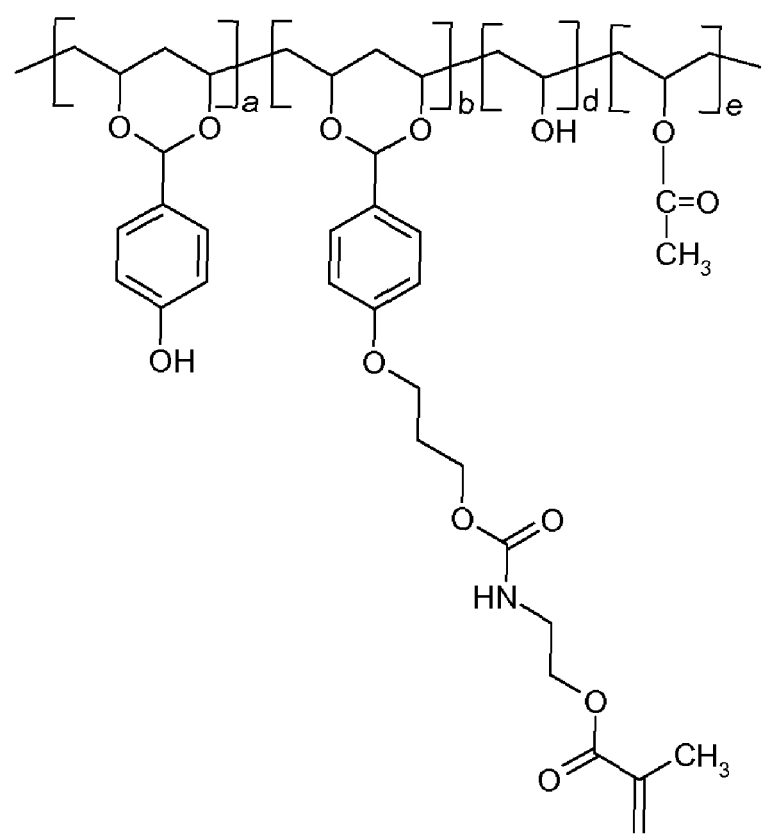
FIG. 16 is the ideal structure of polymer binder RPB-03.

The reactive polymer binder RPB-03 was synthesized by adding, by portions, 90 grams of polyvinyl alcohol (Celvol™ 103, a 98% hydrolyzed polyvinyl acetate having an average molecular weight of about 18,000) to a reaction flask containing 500 grams of dimethylsulfoxide (DMSO) at 60° C., under nitrogen atmosphere and with constant stirring. After complete dissolution, 3 ml of concentrated sulfuric acid, which acts as a catalyst for this reaction, were added to the flask. After thirty minutes, 12.2 grams of 4-hydroxybenzaldehyde (100 mmole, available from Sigma-Aldrich, Canada) were slowly added to the flask and the mixture was stirred at 60° C. for 4 hours. Then, 0.5 gram of sodium hydride (60% in mineral oil, available from Sigma-Aldrich, Canada) was slowly added into the reaction. After hydrogen gas was no longer produced from the reaction, 3.0 grams of 3-bromopropylmethacryloyl-ethyl carbamate was added into the reaction mixture. The reaction was continued for 5 hours at 60° C. The product was precipitated in de-ionized water, filtered and washed copiously with de-ionized water. It was then dried in air until constant weight. The ideal structure of RPB-03 is shown in FIG. 16, wherein a=9.00%, b=1.00%, d=88.00% and e=2.00%.

EXAMPLE 14

Figure 17:
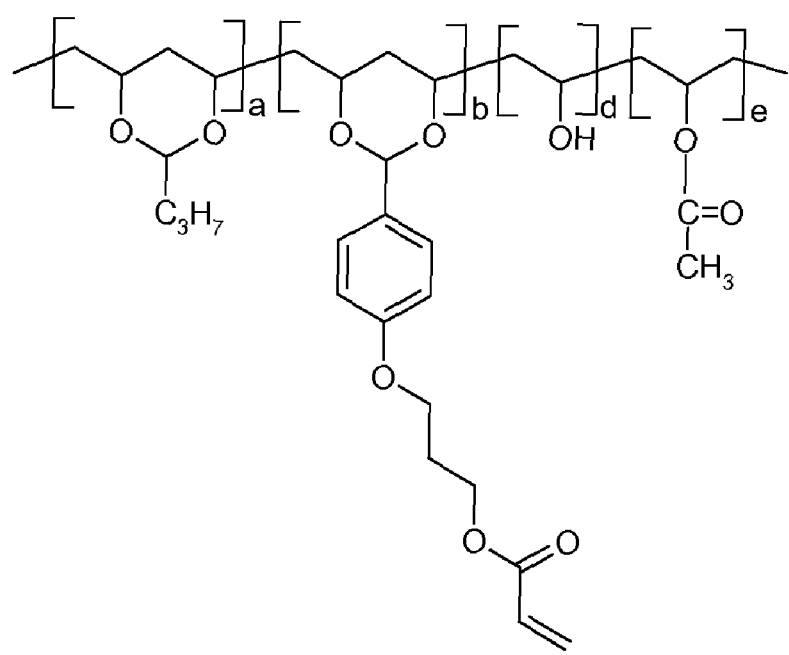
FIG. 17 is the ideal structure of polymer binder RPB-04.

The reactive polymer binder RPB-04 was synthesized by adding, by portions, 90 grams of polyvinyl alcohol (Celvol™ 103, a 98% hydrolyzed polyvinyl acetate having an average molecular weight of about 18,000) to a reaction flask containing 500 grams of dimethylsulfoxide (DMSO) at 60° C., under nitrogen atmosphere and with constant stirring. After complete dissolution, 3 ml of concentrated sulfuric acid, which acts as a catalyst for this reaction, were added to the flask. After thirty minutes, 6.5 grams of butyraldehyde and 2.35 grams of acryloyl-propyloxybenzaldehyde (available from American Dye Source Inc., Canada) were added into the reaction mixture. The reaction was continued for 5 hours at 60° C. The product was precipitated in de-ionized water, filtered and washed copiously with de-ionized water. It was then dried in air until constant weight. The ideal structure of RPB-04 is shown in FIG. 17, wherein a=9.00%, b=1.00%, d=88.00% and e=2.00%.

EXAMPLE 15

Figure 18:
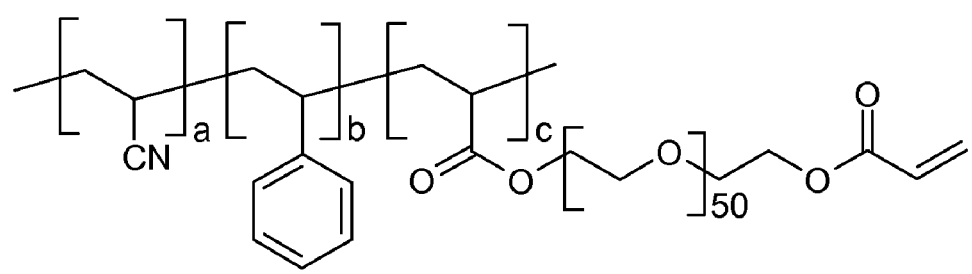
FIG. 18 is the ideal structure of polymer binder RPB-05.

The reactive polymer binder, RPB-05 was synthesized by heating a mixture of 200 grams of anhydrous 1,3-dioxolane, dissolving with 15.0 g poly(ethylene glycol) acrylate (Mn~2,010, available from American Dye Source Inc., Canada), 15.0 g styrene, 50.0 g acrylonitrile and in a 1L 4-neck flask at 75° C. under a nitrogen atmosphere and constant stirring. After heating for 30 minutes, 0.5 g of Vazo™ 64 was added to the reaction mixture. After 10 hours of polymerization at 75° C., another 0.5 g of Vazo™ 64 was added into the reaction mixture and the polymerization was continued for another 14 hours. Air was introduced into the reaction mixture and it stirring at 75° C. continued for an additional 2 hours to terminate the polymerization. The reaction temperature was lowered to 5° C. and 4 grams of triethylamine were added into the reaction mixture. Then, a solution containing 10 grams of 1,3-dioxolane and 2 grams of acryloyl chloride was slowly introduced into the reaction. The reaction was stirred at room temperature for 5 hours. The product was precipitated in water and dried until constant weight. The molecular weight of RPB-03 was determined to be around 28,000 with a polymer dispersity of 1.4. The ideal structure of RPB-05 is shown in FIG. 18, wherein a=86.16%, b=13.16% and c=0.68%.

An emulsion of RPB-05 was prepared by slowly adding 50 grams of de-ionized water into 200 grams n-propanol solution, in which 80 grams of RPB-03 were dissolved, using a high shear mixer set at 7,500 rpm.

EXAMPLE 16

Figure 19:
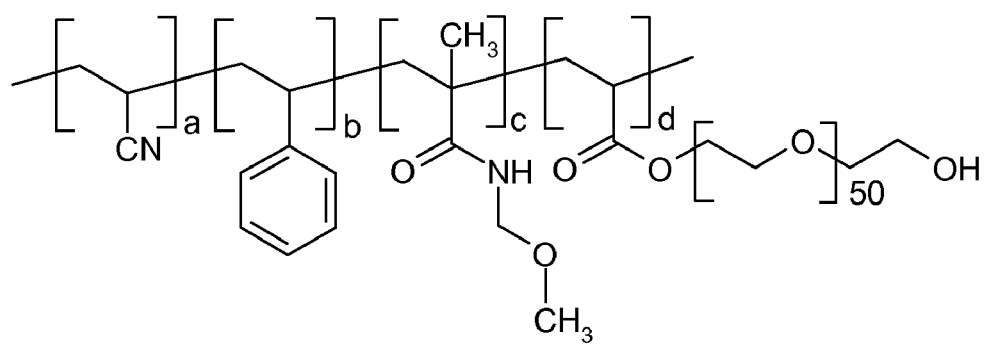
FIG. 19 is the ideal structure of polymer binder RPB-06.
Figure 20:
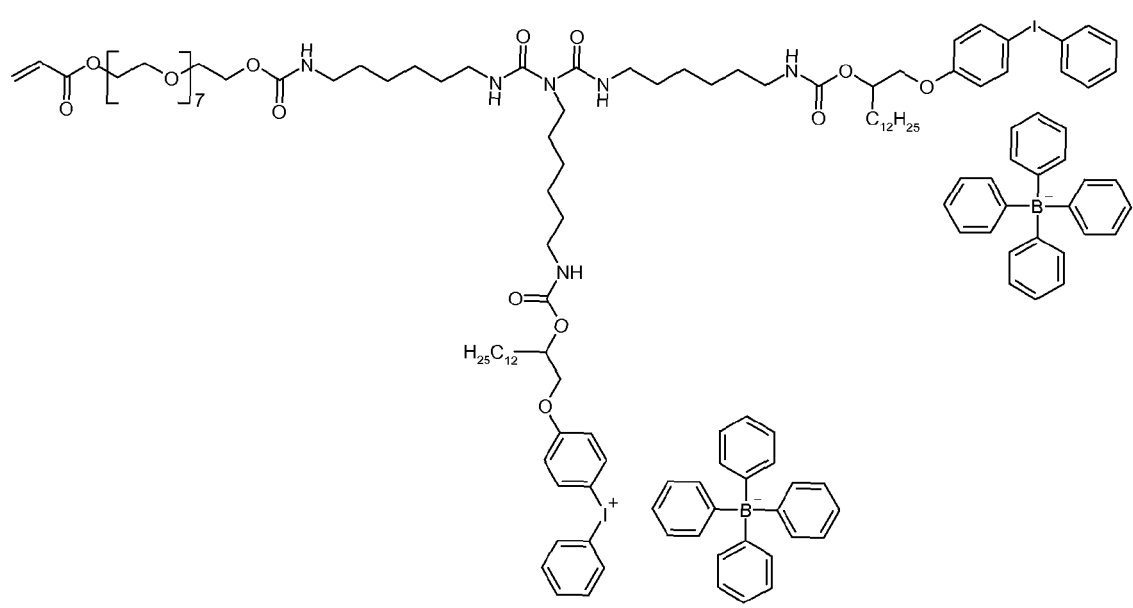
FIG. 20 is the possible structure of a specific embodiment of an iodonium salt of the present invention.
Figure 21:
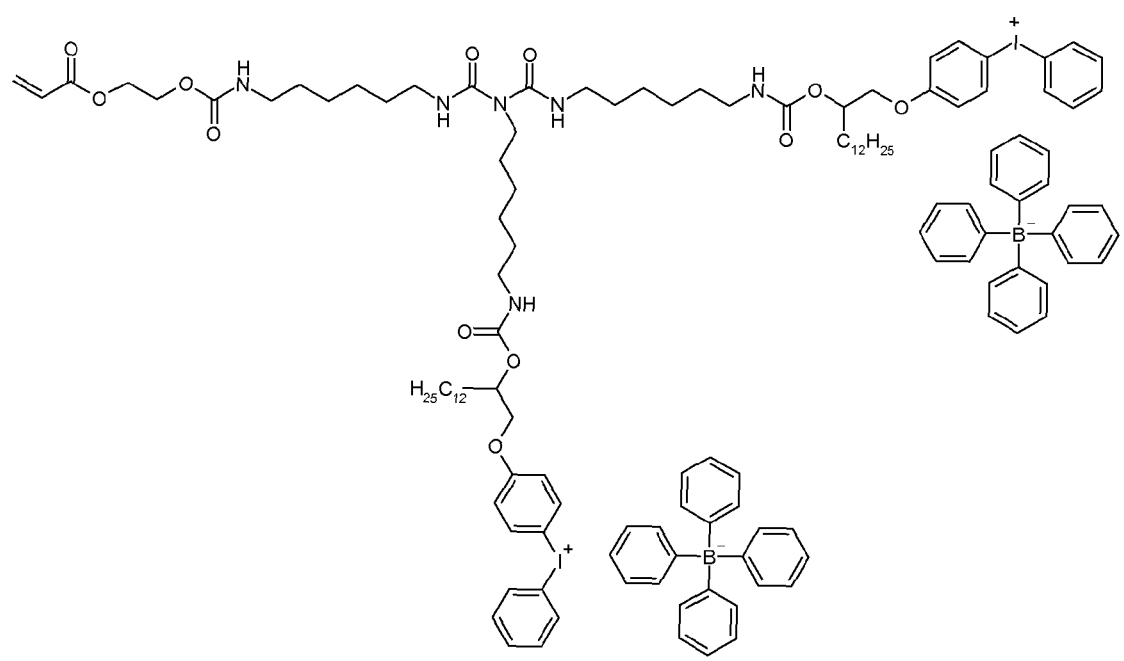
FIG. 21 is the possible structure of a specific embodiment of an iodonium salt of the present invention.
Figure 22:
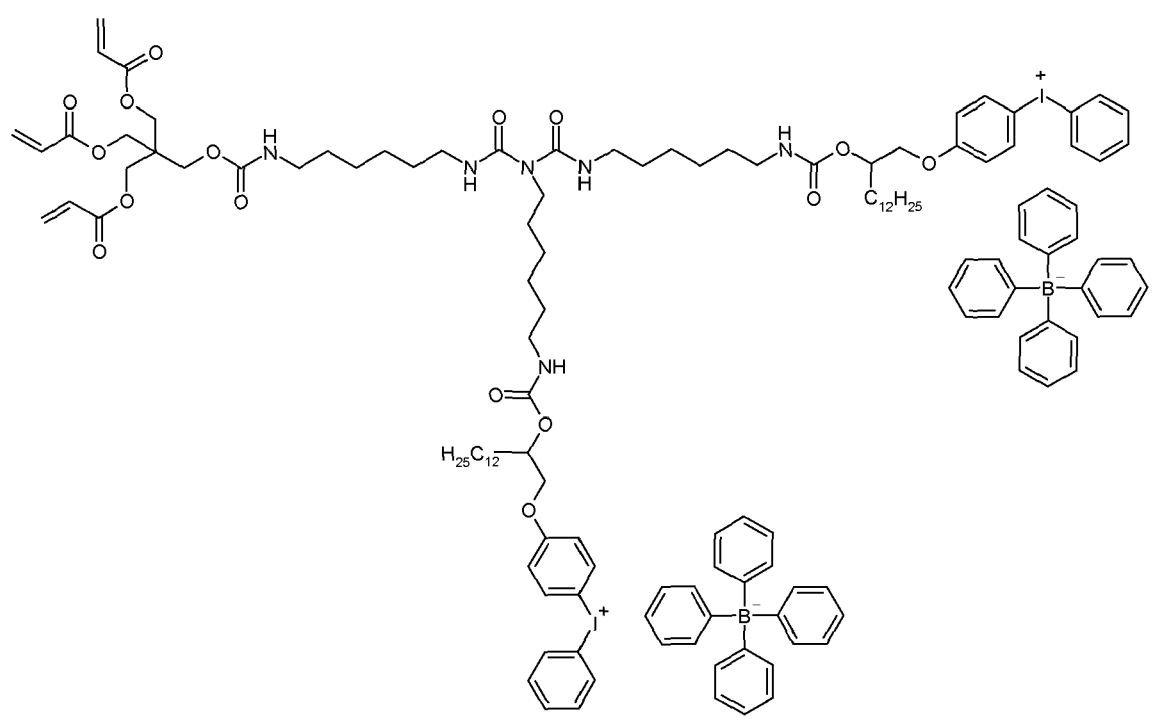
FIG. 22 is the possible structure of a specific embodiment of an iodonium salt of the present invention.
Figure 23:
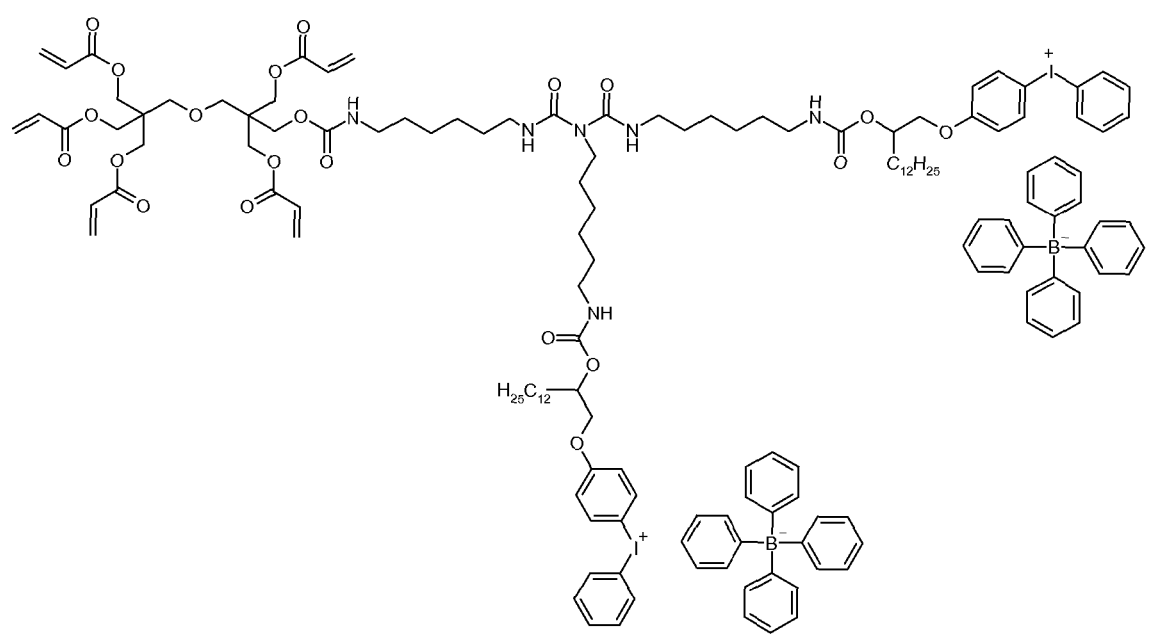
FIG. 23 is the possible structure of a specific embodiment of an iodonium salt of the present invention.
Figure 24:
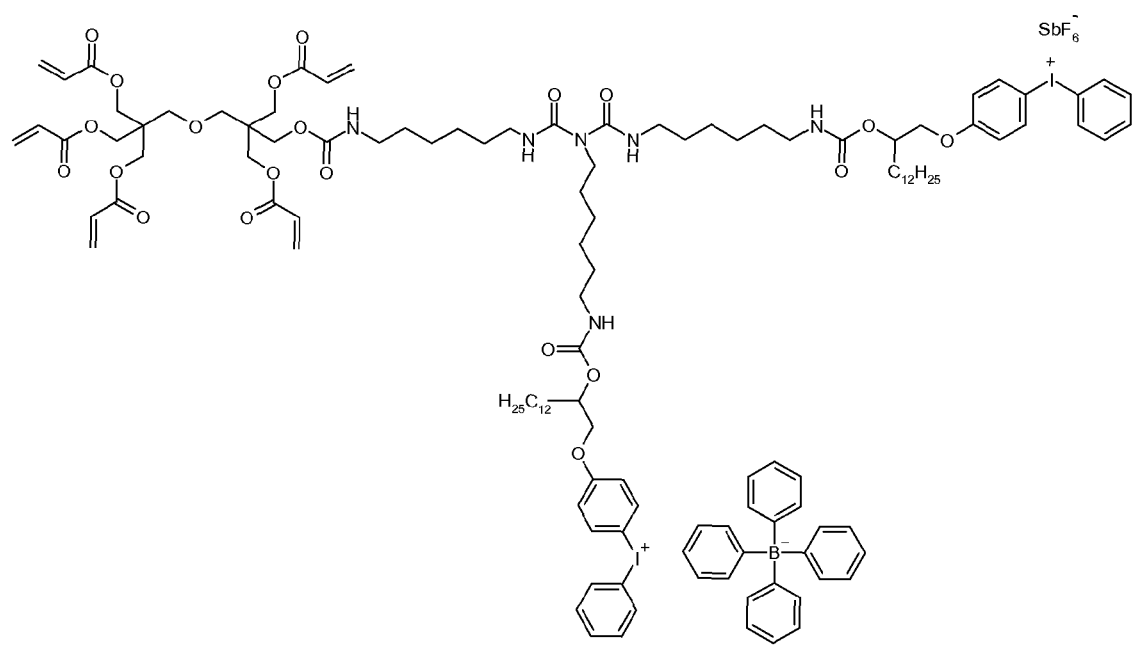
FIG. 24 is the possible structure of a specific embodiment of an iodonium salt of the present invention.
Figure 25:
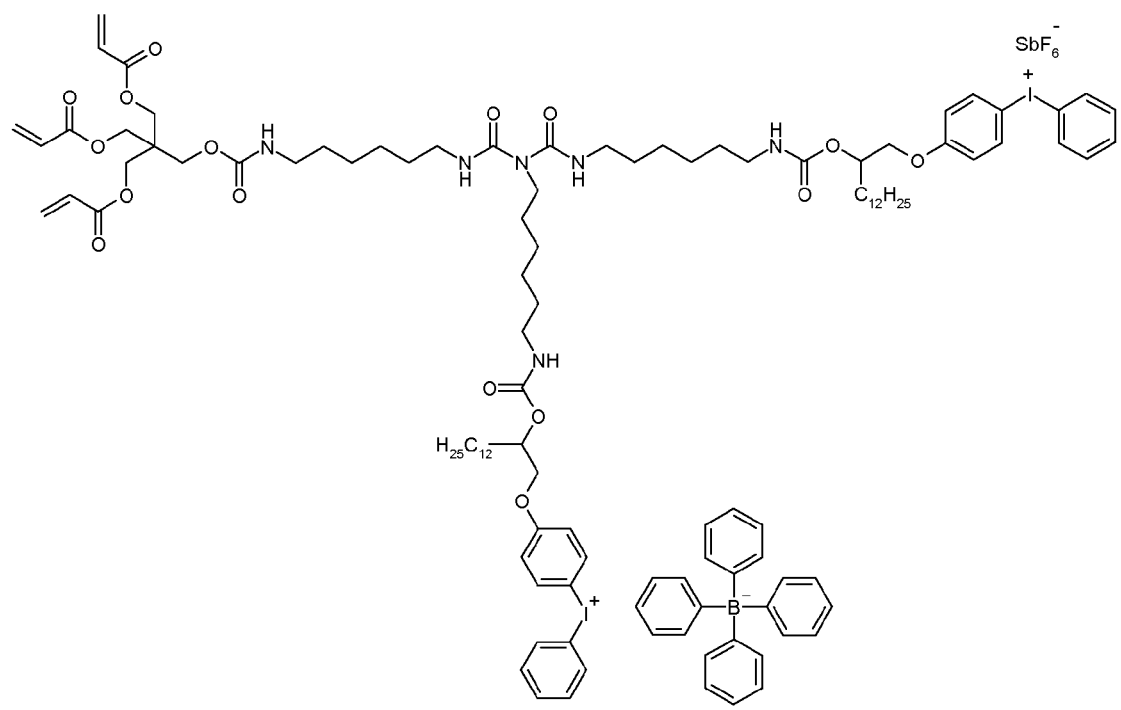
FIG. 25 is the possible structure of a specific embodiment of an iodonium salt of the present invention.

The reactive polymer binder, RPB-06 was synthesized by heating a mixture of 200 grams of n-propanol and 50 grams of de-ionized water, which in which 15.0 g poly(ethylene glycol) acrylate (Mn ~2,000, available from American Dye Source Inc., Canada) were dissolved, 5.0 grams of N-methoxymethylmethacrylamide (available from American Dye Source Inc., Canada), 15.0 g styrene and 50.0 g acrylonitrile, in a 1L 4-neck flask at 75° C. under a nitrogen atmosphere and constant stirring. After heating for 30 minutes, 0.5 g of Vazo™ 64 was added into the reaction mixture. The solution became hazy within 30 minutes of polymerization. After polymerization for 10 hours at 75° C., another 0.5 g of Vazo™ 64 was added into the reaction mixture and the polymerization was continued for another 14 hours. Air was introduced into the reaction mixture and stirring at 75° C. was continued for an additional 2 hours to terminate the polymerization. The molecular weight of RPB-06 was determined to be around 29,000 with polymer dispersity of 1.7. The ideal structure of RPB-06 is shown in FIG. 19, wherein a=82.88%, b=12.66%, c=3.81% and d=0.65%.

On-Press Developable Negative-Working Lithographic Printing Plates

EXAMPLE 17

A coating solution with the following composition was coated on a brush-grained, phosphoric acid anodized aluminum substrate using wire-wound rod and dried at 80° C. with hot air. The obtained coating weight was around 1.0 g/m$^2$.

| Composition | From example | % by Solid Weight |
|---|---|---|
| PVA-01 | 1 | 2.00 |
| Iodonium Salt Mixture | 9 | 5.00 |
| RPB-01 | 10 | 0.50 |
| RPB-05 | 14 | 2.15 |
| 3-Mercapto triazol | | 0.25 |
| Blue Color Former(*) | | 0.10 |
| n-Propanol | | 90.0 |
| Water | | 10.0 |
| BYK 336 | | 0.10 |

(*)Blue Color Former is Blue-63 (available from Yamamoto Chemicals Inc., Japan)

The plate was imaged between 100 and 250 mJ/cm$^2$ and mounted on the AB Dick press. High quality printing image was obtained on paper after 10 impressions. The plate can be used to print more than 20,000 high-resolution copies.

EXAMPLE 18

A coating solution with the following composition was coated on a brush-grained, phosphoric acid anodized aluminum substrate using wire-wound rod and dried at 80° C. with hot air. The obtained coating weight was around 1.0 g/m$^2$.

| Composition | From example | % by Solid Weight |
|---|---|---|
| PVA-02 | 2 | 2.00 |
| Iodonium Salt Mixture | 9 | 5.00 |
| RPB-01 | 10 | 0.50 |
| RPB-05 | 14 | 2.15 |
| 3-Mercapto triazol | | 0.25 |
| Blue Color Former(*) | | 0.10 |
| n-Propanol | | 90.0 |
| Water | | 10.0 |
| BYK 336 | | 0.10 |

(*)Blue Color Former is Blue-63 (available from Yamamoto Chemicals Inc., Japan)

The plate was imaged between 100 and 250 mJ/cm$^2$ and mounted on the AB Dick press. High quality printing image was obtained on paper after 10 impressions. The plate can be used to print more than 20,000 high-resolution copies.

EXAMPLE 19

A coating solution with the following composition was coated on a brush-grained, phosphoric acid anodized aluminum substrate using wire-wound rod and dried at 80° C. with hot air. The obtained coating weight was around 1.0 g/m$^2$.

| Composition | From example | % by Solid Weight |
|---|---|---|
| PVA-01 | 1 | 2.00 |
| Iodonium Salt Mixture | 9 | 5.00 |
| RPB-01 | 10 | 0.50 |
| RPB-06 | 15 | 2.15 |
| 3-Mercapto triazol | | 0.25 |
| Blue Color Former(*) | | 0.10 |
| n-Propanol | | 90.0 |
| Water | | 10.0 |
| BYK 336 | | 0.10 |

(*)Blue Color Former is Blue-63 (available from Yamamoto Chemicals Inc., Japan)

The plate was imaged between 100 and 250 mJ/cm$^2$ and mounted on the AB Dick press. High quality printing image was obtained on paper after 10 impressions. The plate can be used to print more than 20,000 high-resolution copies.

EXAMPLE 20

A coating solution with the following composition was coated on a brush-grained, phosphoric acid anodized aluminum substrate using wire-wound rod and dried at 80° C. with hot air. The obtained coating weight was around 1.0 g/m$^2$.

| Composition | From example | % by Solid Weight |
|---|---|---|
| PVA-01 | 1 | 2.00 |
| Iodonium Salt Mixture | 9 | 5.00 |
| RPB-01 | 10 | 1.00 |
| RPB-03 | 15 | 1.65 |
| 3-Mercapto triazol | | 0.25 |
| Blue Color Former(*) | | 0.10 |
| n-Propanol | | 90.0 |
| Water | | 10.0 |
| BYK 336 | | 0.10 |

(*)Blue Color Former is Blue-63 (available from Yamamoto Chemicals Inc., Japan)

The plate was imaged between 100 and 250 mJ/cm$^2$ and mounted on the AB Dick press. High quality printing image was obtained on paper after 10 impressions. The plate can be used to print more than 20,000 high-resolution copies.

EXAMPLE 21

A coating solution with the following composition was coated on a brush-grained, phosphoric acid anodized aluminum substrate using wire-wound rod and dried at 80° C. with hot air. The obtained coating weight was around 1.0 g/m².

| Composition | From example | % by Solid Weight |
|---|---|---|
| PVA-01 | 1 | 2.00 |
| Iodonium Salt Mixture | 9 | 5.00 |
| RPB-01 | 10 | 1.00 |
| RPB-04 | 15 | 1.65 |
| 3-Mercapto triazol | | 0.25 |
| Blue Color Former(*) | | 0.10 |
| n-Propanol | | 90.0 |
| Water | | 10.0 |
| BYK 336 | | 0.10 |

(*)Blue Color Former is Blue-63 (available from Yamamoto Chemicals Inc., Japan)

The plate was imaged between 100 and 250 mJ/cm² and mounted on the AB Dick press. High quality printing image was obtained on paper after 10 impressions. The plate can be used to print more than 20,000 high-resolution copies.

Although the present invention has been described hereinabove by way of specific embodiments thereof, it can be modified, without departing from the spirit and nature of the subject invention as defined in the appended claims

What is claimed is:

1. An iodonium salt comprising a positively charged iodine atom to which two aryl rings are attached and a negatively charged counter ion,
the iodonium salt having attached to at least one of said aryl rings at least one urethane- and/or urea-containing substituent, said substituent having attached thereto at least one functional group capable of undergoing cationic or radical polymerization
the iodonium salt being of general formula:

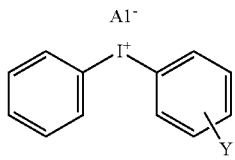

wherein A1⁻ is said negatively charged counter ion, Y is said substituent, and each of the aryl rings is optionally substituted.

2. The iodonium salt of claim 1 wherein said functional group is acrylate, methacrylate or vinyl ether.

3. The iodonium salt of claim 1 having as a general formula:

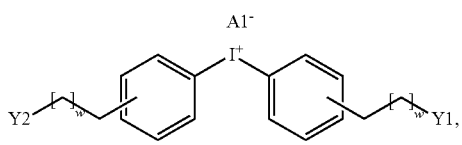

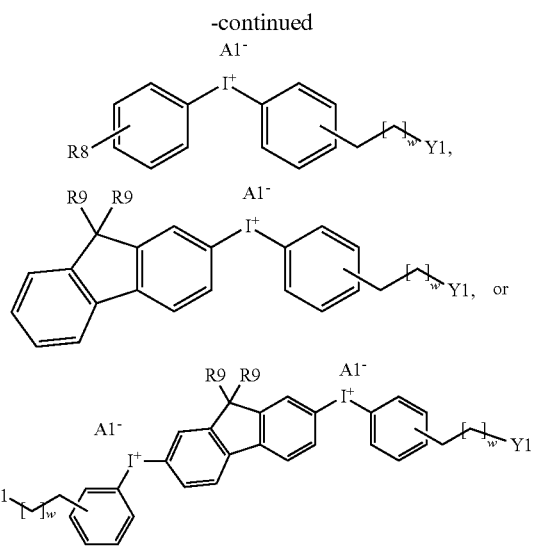

wherein:
A1 is a tosylate, triflate, hexafluoroantimonate, tetrafluoroborate, tetraphenylborate or triphenyl-n-alkylborate anionic counter ion;
w may vary between 0 and 18;
R8 and R9 are independently hydrogen, linear $C_1$-$C_{18}$ alkyl, branched $C_1$-$C_{18}$ alkyl, alkyl oxy, poly(ethylene oxide) or poly(propylene oxide); and
Y1 and Y2 each independently represent said urethane- and/or urea-containing substituent having attached thereto said functional group.

4. The iodonium salt of claim 1 having as a general formula:

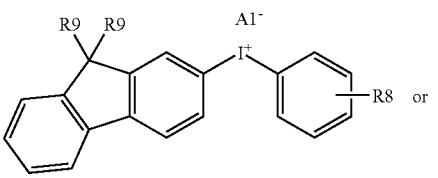

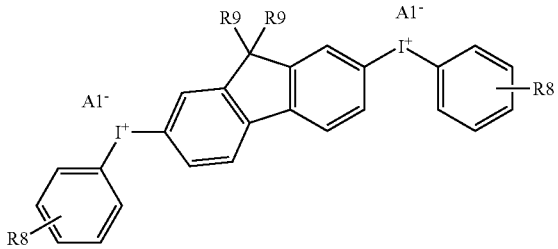

wherein:
A1 represents a tosylate, triflate, hexafluoroantimonate, tetrafluoroborate, tetraphenylborate and triphenyl-n-alkylborate anionic counter ion; and
R8 and R9 are independently hydrogen, linear $C_1$-$C_{18}$alkyl, branched $C_1$-$C_{18}$alkyl, alkyl oxy, poly(ethylene oxide) or poly(propylene oxide),
and wherein at least one of R8 or R9 is not hydrogen and represents, alone in the case of R8 and together with the carbon atom to which it is attached in the case of R9, said urethane- and/or urea-containing substituent having attached thereto said functional group.

5. A lithographic printing plate coating solution comprising the iodonium Salt of claim 1 or a mixture thereof.

6. The coating solution of claim 5 further comprising a near infrared absorbing dye.

7. The coating solution of claim 6 wherein said near infrared absorbing dye is a first acetal copolymer or a mixture thereof.

8. The coating solution of claim 7 wherein said first acetal copolymer has attached thereto at least one second functional group capable of undergoing cationic or radical polymerization.

9. The coating solution of claim 7 wherein the first acetal copolymer has the following structure:

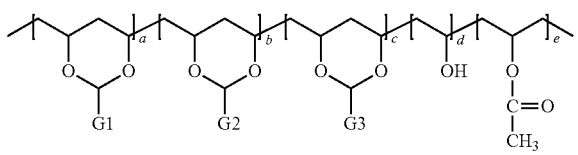

wherein:
G1 represents a processing segment providing solubility in organic solvents;
G2 represents a thermal reactive segment;
G3 represents a radiation-absorbing segment exhibiting one or more strong absorption peaks between 700 and 1100 nm;
a, b, c, d and e are molar ratios and may vary from 0.01 to 0.99;
any of

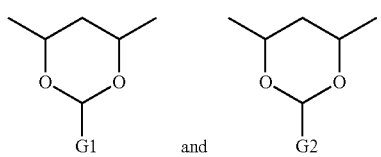

may independently be replaced by

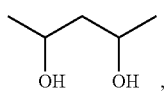

and
a second functional group capable of undergoing cationic or radical polymerization may optionally be attached to G2 or G3.

10. The coating solution of claim 9 wherein G1 is linear alkyl, branched alkyl, linear aryl or branched aryl, wherein said linear alkyl, branched alkyl, said linear aryl or branched aryl comprise a cyano, hydroxy, dialkylamino, trialkylammonium salts, ethylene oxide, propylene oxide methylbenzylsufonyl-carbamat, carboxylic acid or phosphoric acid functional group.

11. The coating solution of claim 9 wherein G2 is linear alkyl, branched alkyl, linear aryl or branched aryl, wherein said linear alkyl, branched alkyl, linear aryl or branched aryl has attached thereto said second functional group.

12. The coating solution of claim 11 wherein said second functional group is vinyl ether, alkoxy-methyl acrylamide, alkoxy methacrylamide, acrylate or methacrylate.

13. The coating solution of claim 9 wherein G3 is

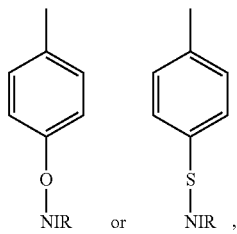

wherein NIR is a near-infrared absorbing chromophore exhibiting one or more strong absorption peaks between 700 and 1100 nm.

14. The coating solution of claim 5 further comprising a polymer binder.

15. The coating solution of claim 14 wherein said polymer binder has attached thereto at least one third functional group capable of undergoing cationic or radical polymerization.

16. The coating solution of claim 15 wherein said third functional group is acrylate, methacrylate, vinyl ether, hydroxyl, alkoxy-methyl acrylamide, alkoxy methacrylamide, N-methoxymethylacrylamide or N-methoxymethylmethacrylamide.

17. The coating solution of claim 14 wherein said polymer binder is a second acetal copolymer of general formula:

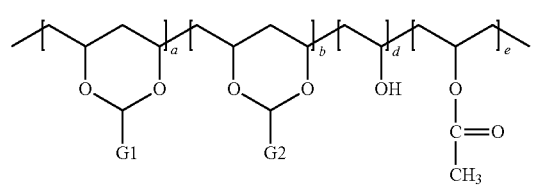

wherein
G1 represents an processing segment providing solubility in organic solvents;
G2 represents an thermal reactive segment;
a, b, d and e are molar ratios and may vary from 0.01 to 0.99; and
any of

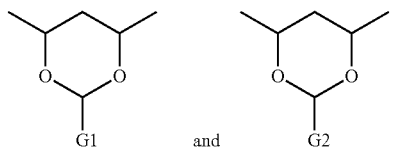

may independently be replaced by

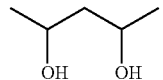

a third functional group capable of undergoing cationic or radical polymerization may optionally be attached to G2.

18. The coating solution of claim 17 wherein G1 is linear alkyl, branched alkyl, linear aryl or branched aryl, wherein said linear alkyl, branched alkyl, linear aryl or branched aryl comprise a cyano, hydroxy, dialkylamino, trialkylammonium salts, ethylene oxide, propylene oxide methylbenzylsufonyl-carbamat, carboxylic acid or phosphoric acid functional group.

19. The coating solution of claim 17 wherein G2 is linear alkyl, branched alkyl, linear aryl or branched aryl, wherein said linear alkyl, branched alkyl, linear aryl or branched aryl has attached thereto said third functional group.

20. The coating solution of claim 15 wherein said polymer binder is selected from the group consisting of solvent-soluble cellulose ether and water-soluble cellulose ether or a mixture thereof, said cellulose ethers having attached thereto said third functional group.

21. The coating solution of claim 20 wherein said polymer binder has the following structure:

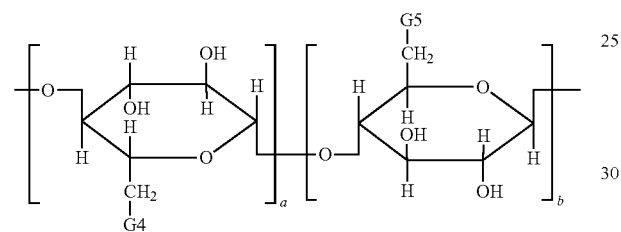

wherein:
a and b are molar ratios and may vary between about 0.01 and about, 0.99,
G4 is hydroxy, hydroxyethyl or hydroxypropyl; and
G5 comprises said third functional group.

22. The coating solution of claim 14 wherein said polymer binder is a copolymer comprising one or more first monomers of formula:

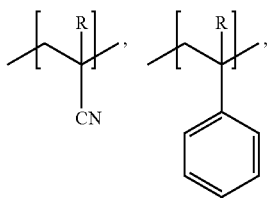

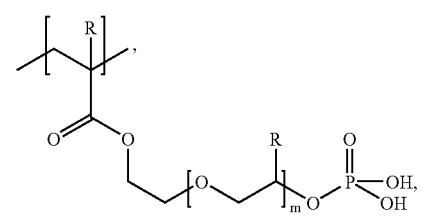

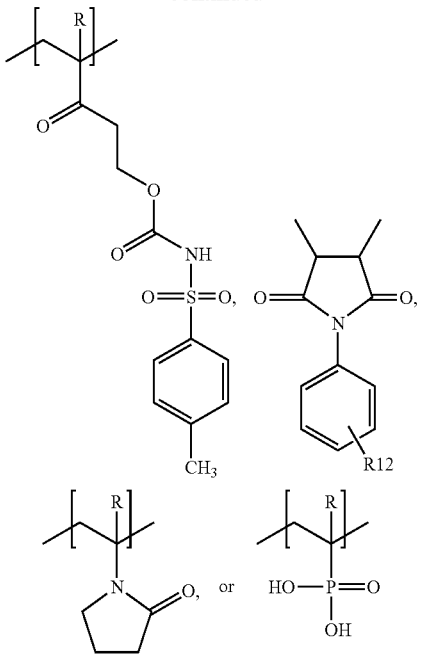

and one or more second monomers of general formula:

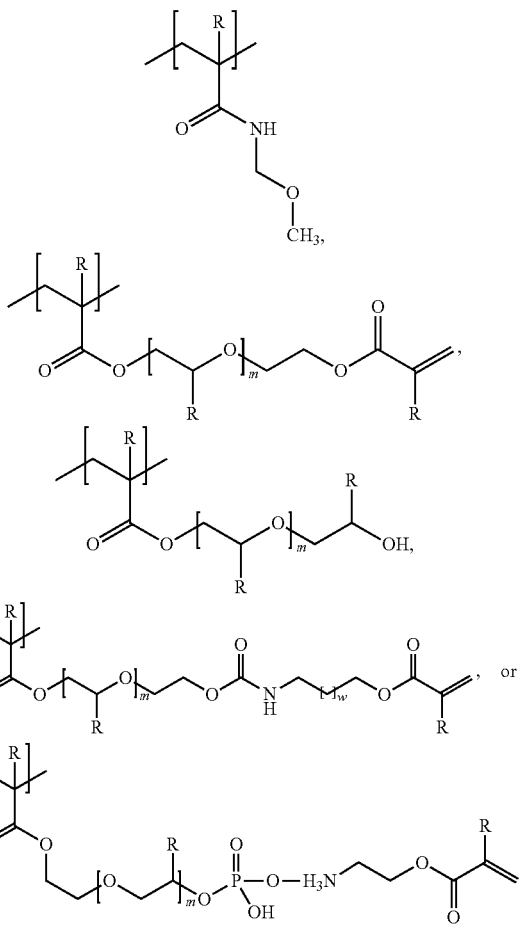

wherein:
m and w may vary between 0 and 50;
R is hydrogen or methyl;
R11 is linear or branched alkyl chain; and
R12 is alkyl, hydroxyl or carboxylic acid.

23. A negative working lithographic printing plate comprising a coating produced by depositing the coating solution of claim 5 onto a substrate.

24. The iodonium salt of claim 3 wherein said functional group is acrylate, methacrylate or vinyl ether.

25. The iodonium salt of claim 4 wherein said functional group is acrylate, methacrylate or vinyl ether.

26. The iodonium salt of claim 3 wherein at least one of R8 or R9 has attached thereto a further functional group capable of undergoing cationic or radical polymerization.

27. The iodonium salt of claim 3 wherein at least one of Y1 or Y2 is:

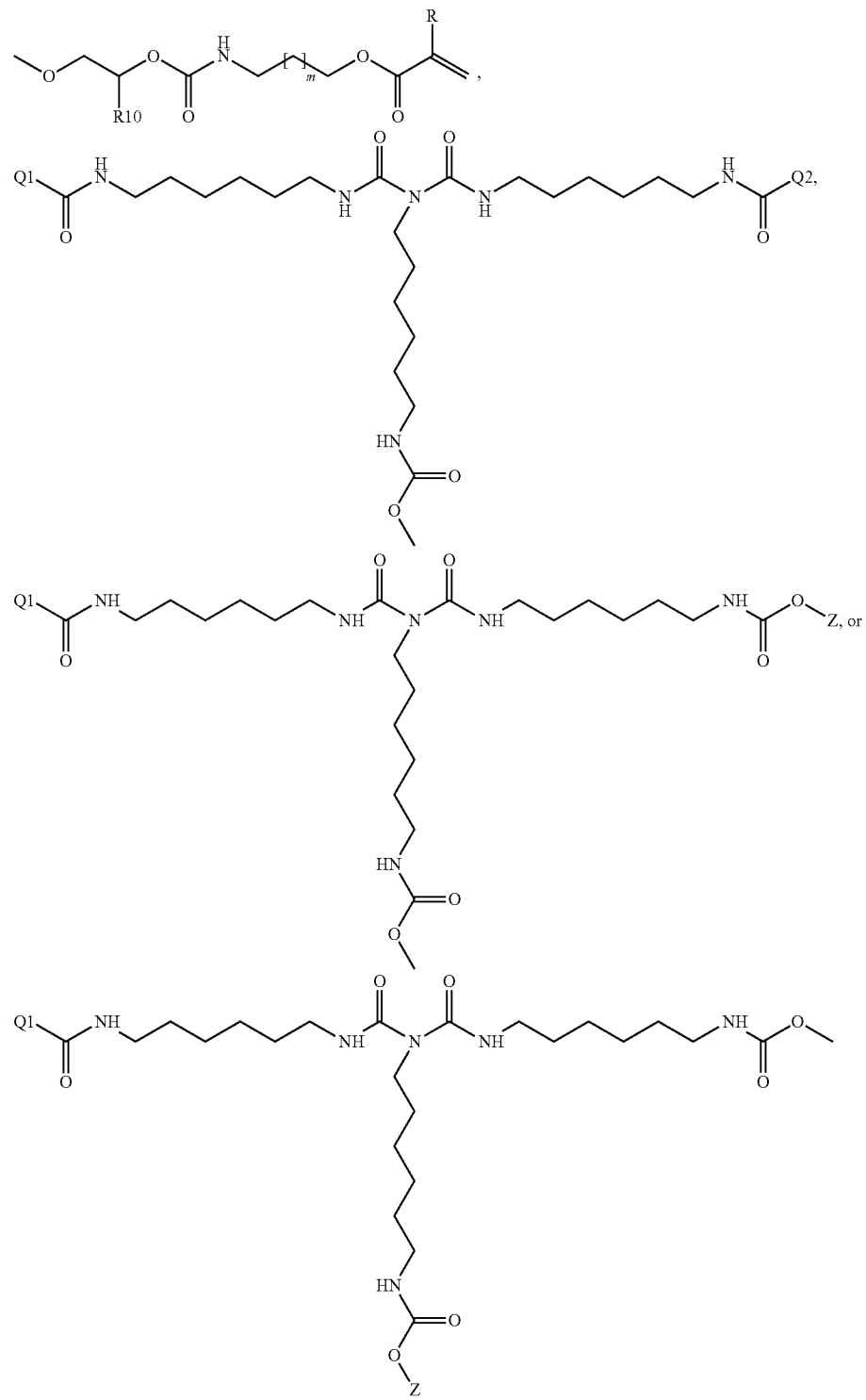

wherein:
R is hydrogen or methyl,
m varies between 1 and 18,
R10 is hydrogen, linear or branched $C_1$-$C_{18}$ alkyl chain;
Q1 and Q2 each independently represent an end compound having attached thereto said functional group; and
Z represents a substituent comprising

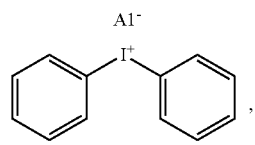

wherein $A1^-$ is as defined in claim 1.

28. The iodonium salt of claim 27 wherein at least one of Q1 or Q2 is:

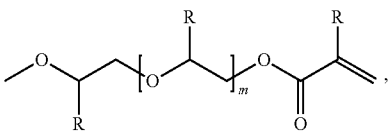

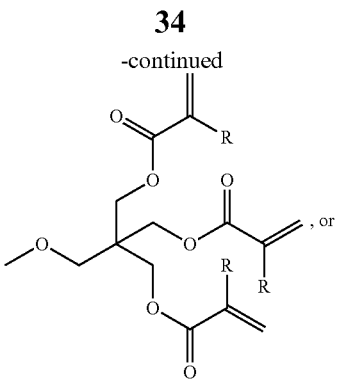

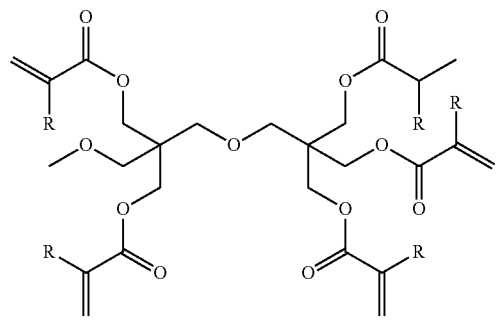

wherein R is hydrogen or methyl and m is as defined in claim 27, and is preferably between 0 and 7.

29. The iodonium salt of claim 28 being:

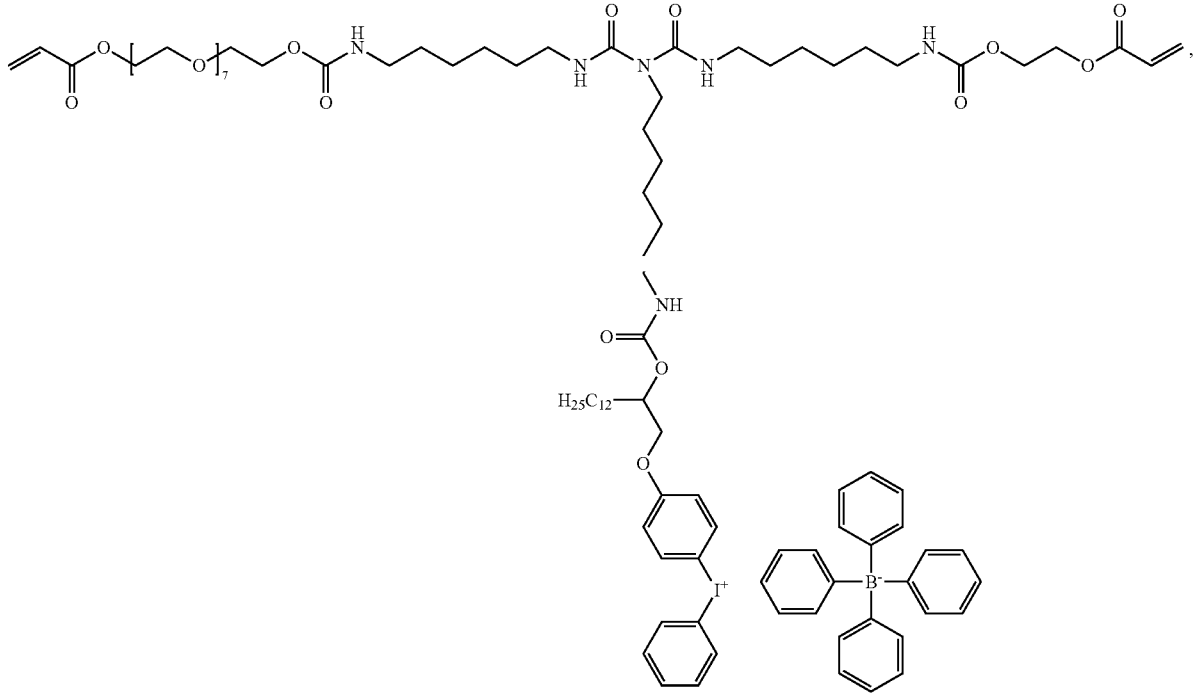

35 36
-continued
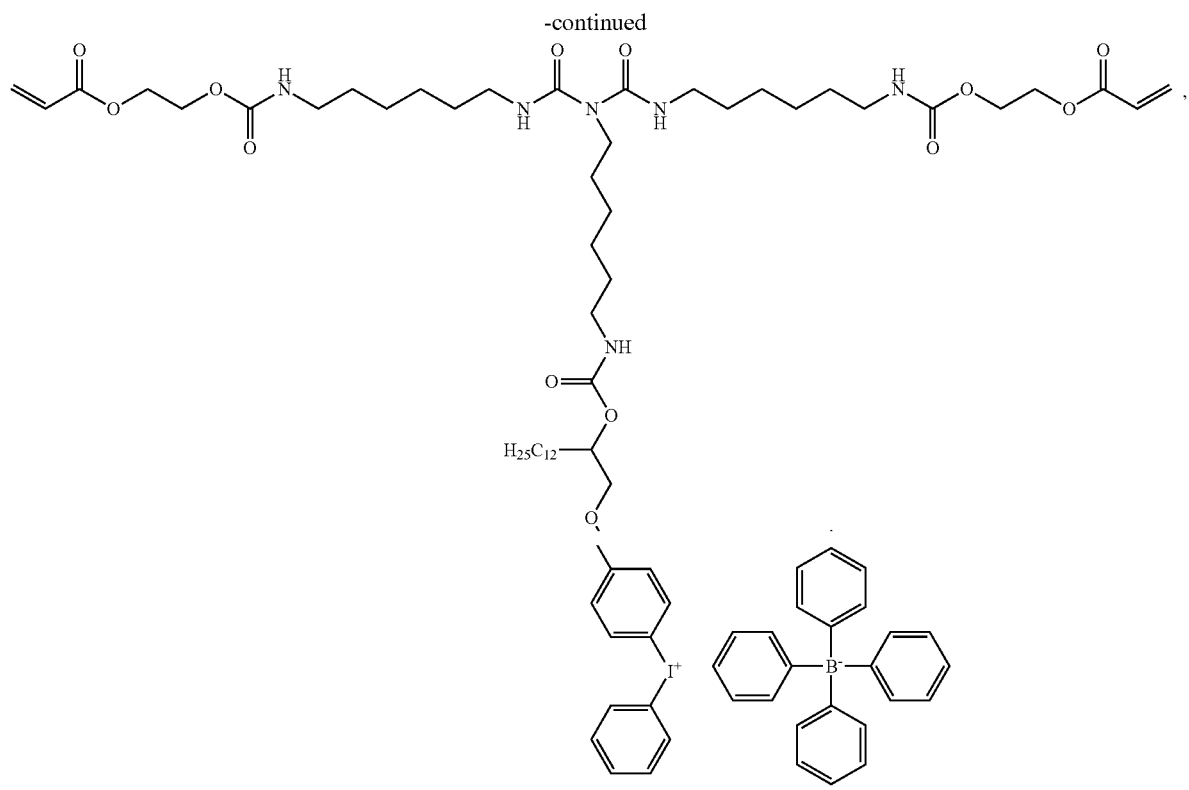
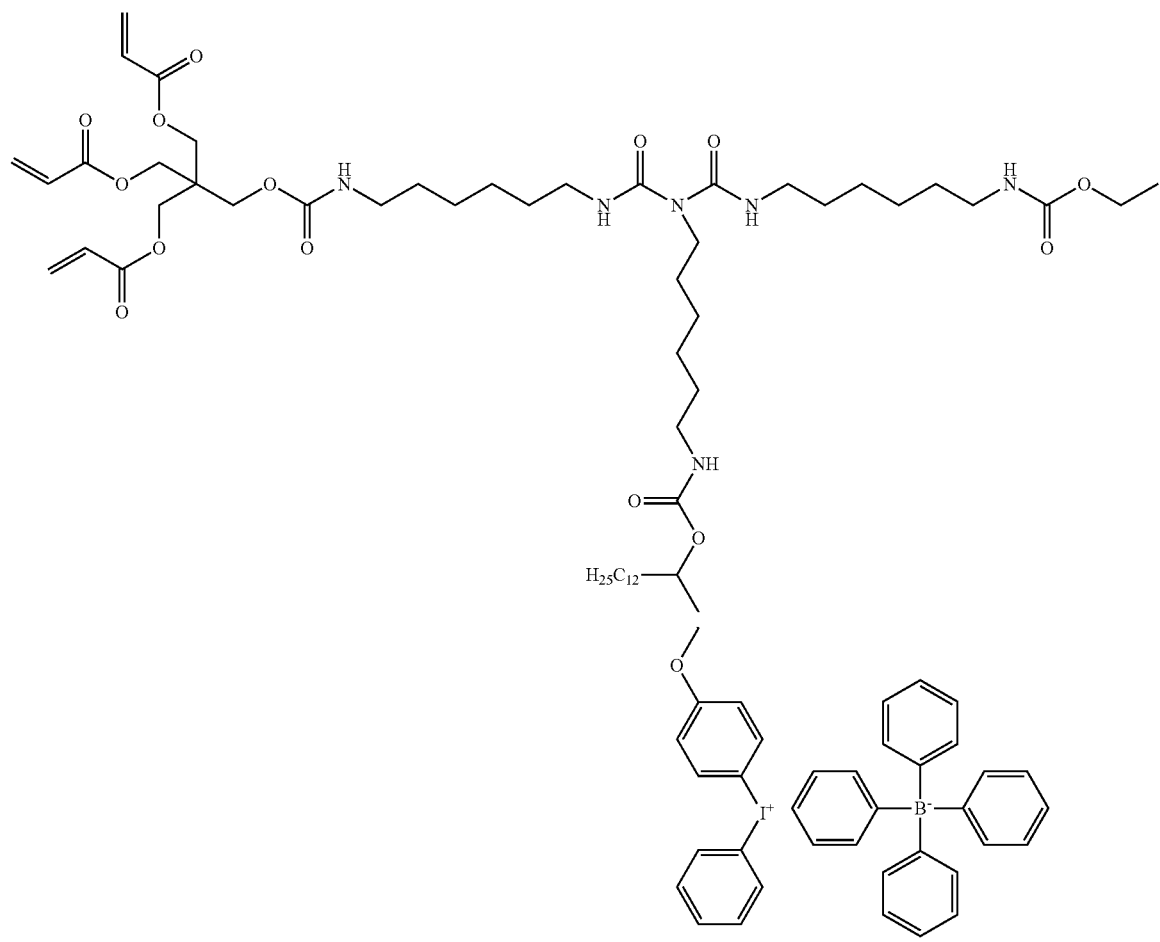

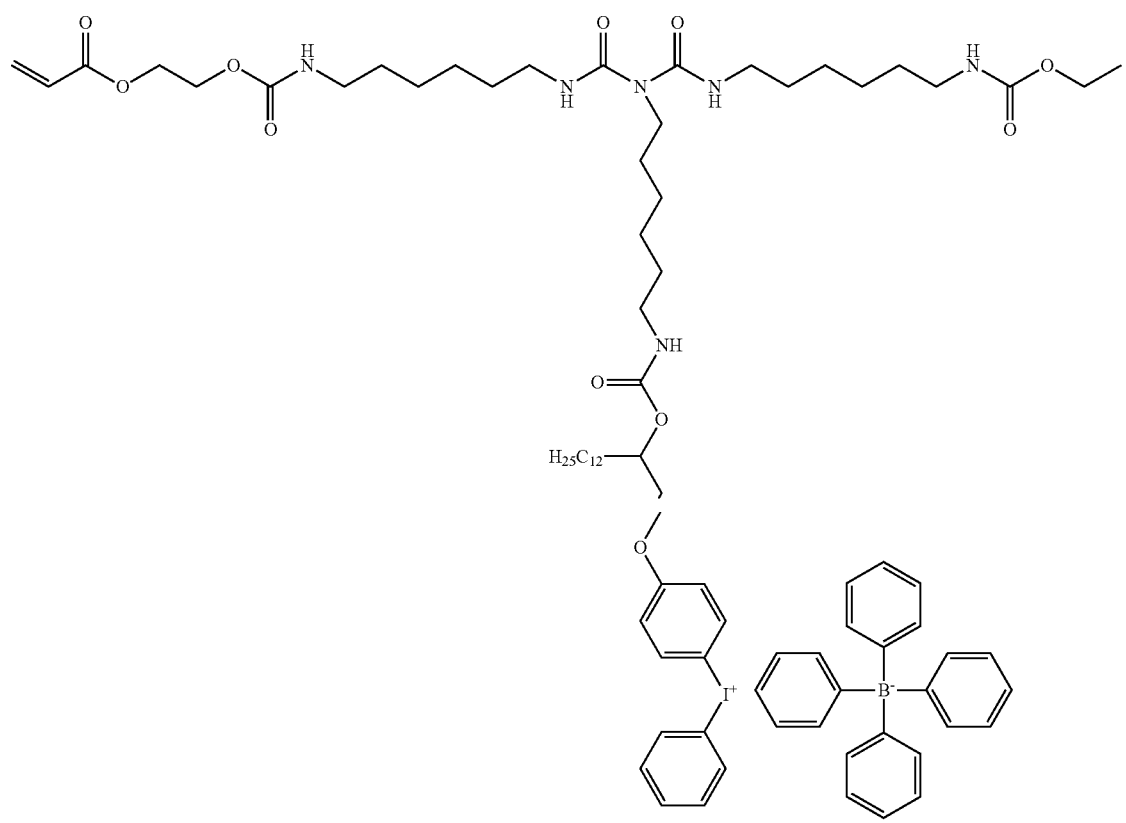
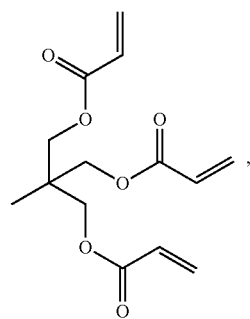

-continued
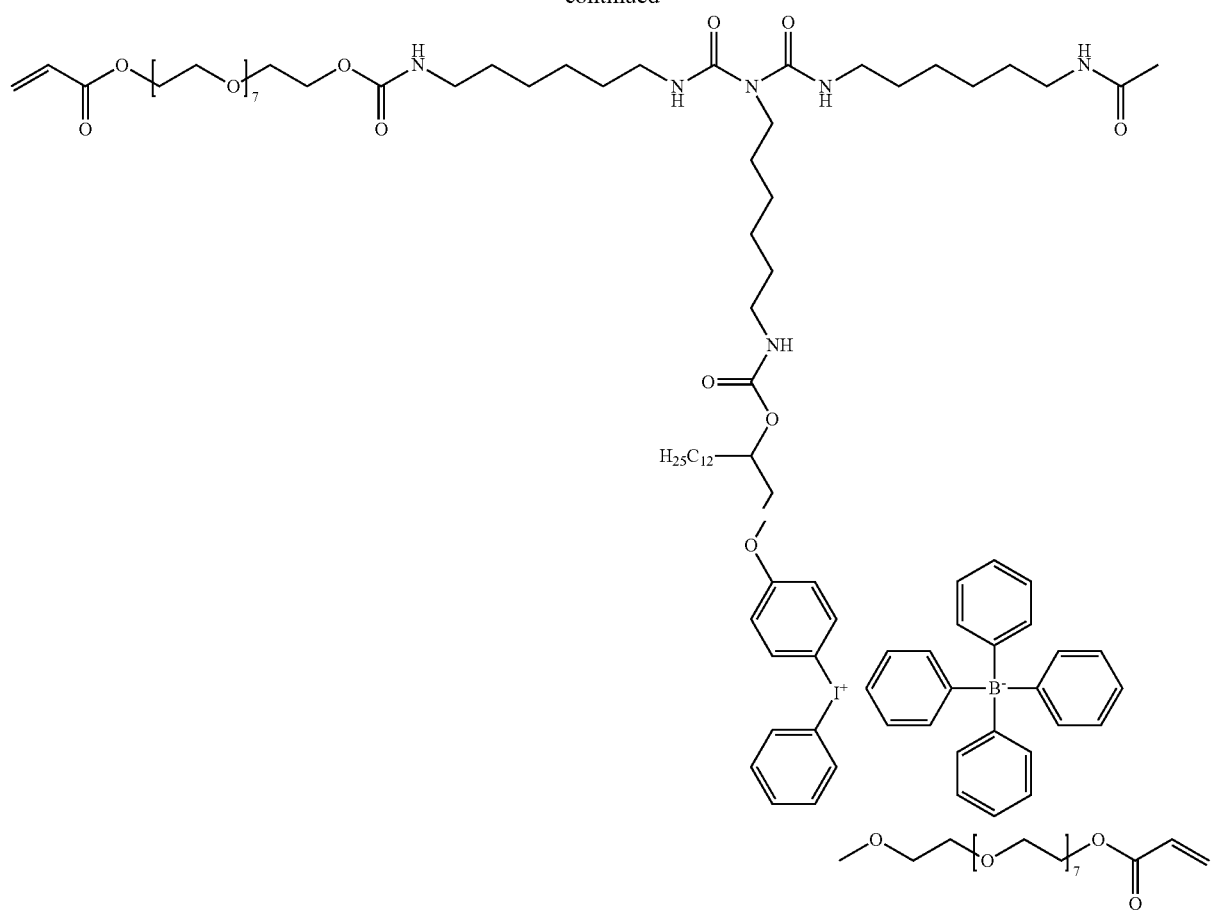
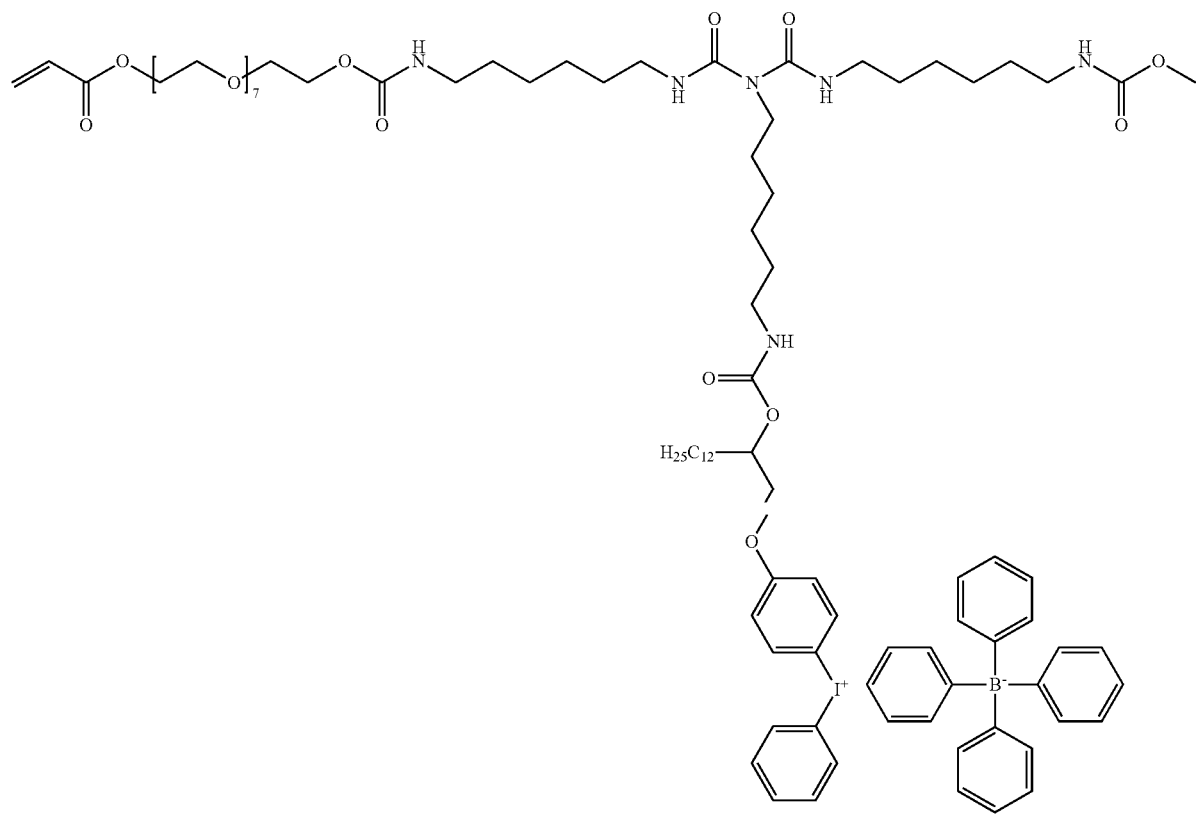

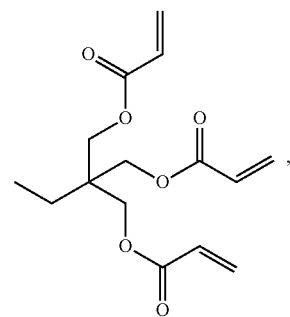
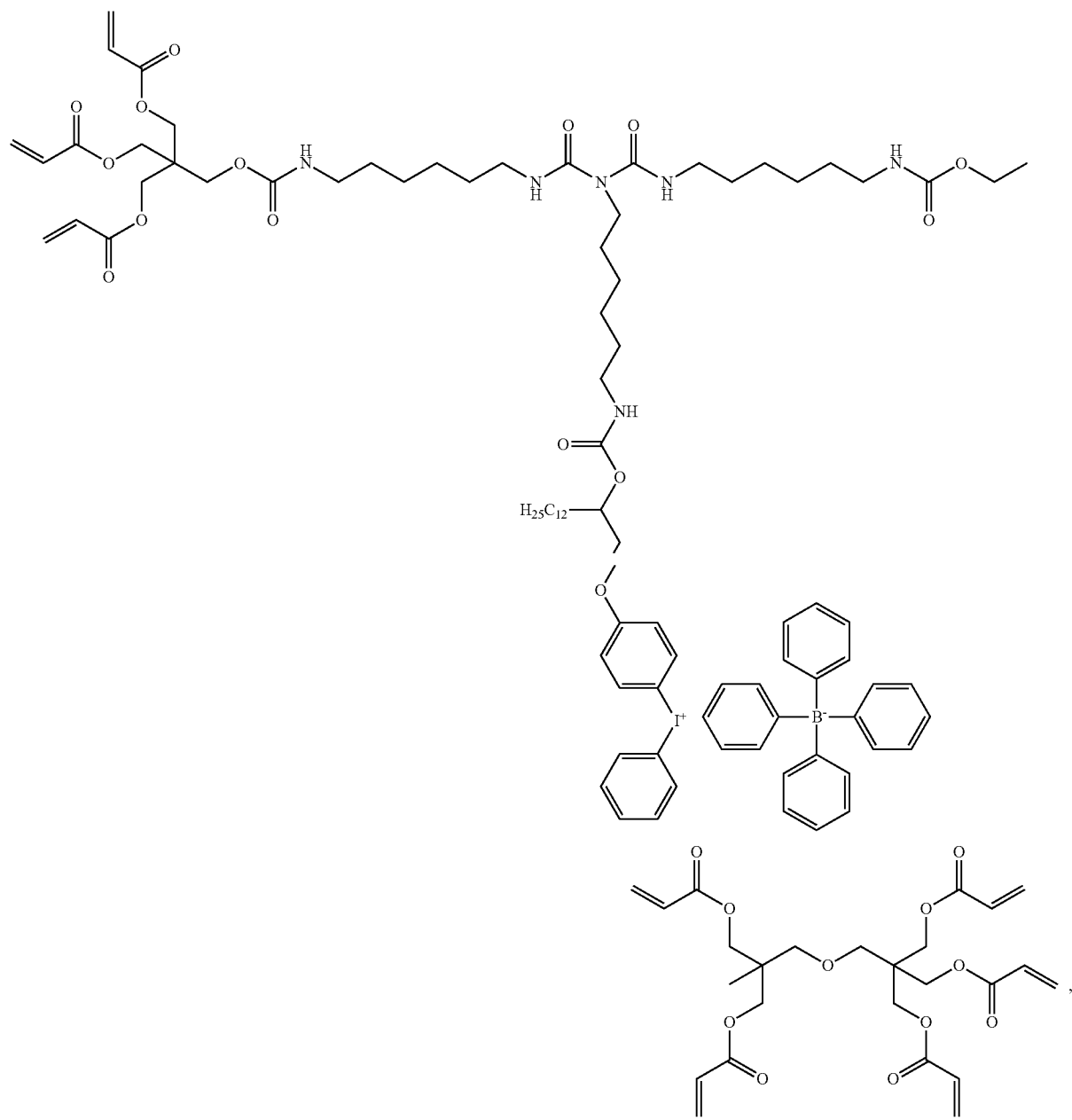

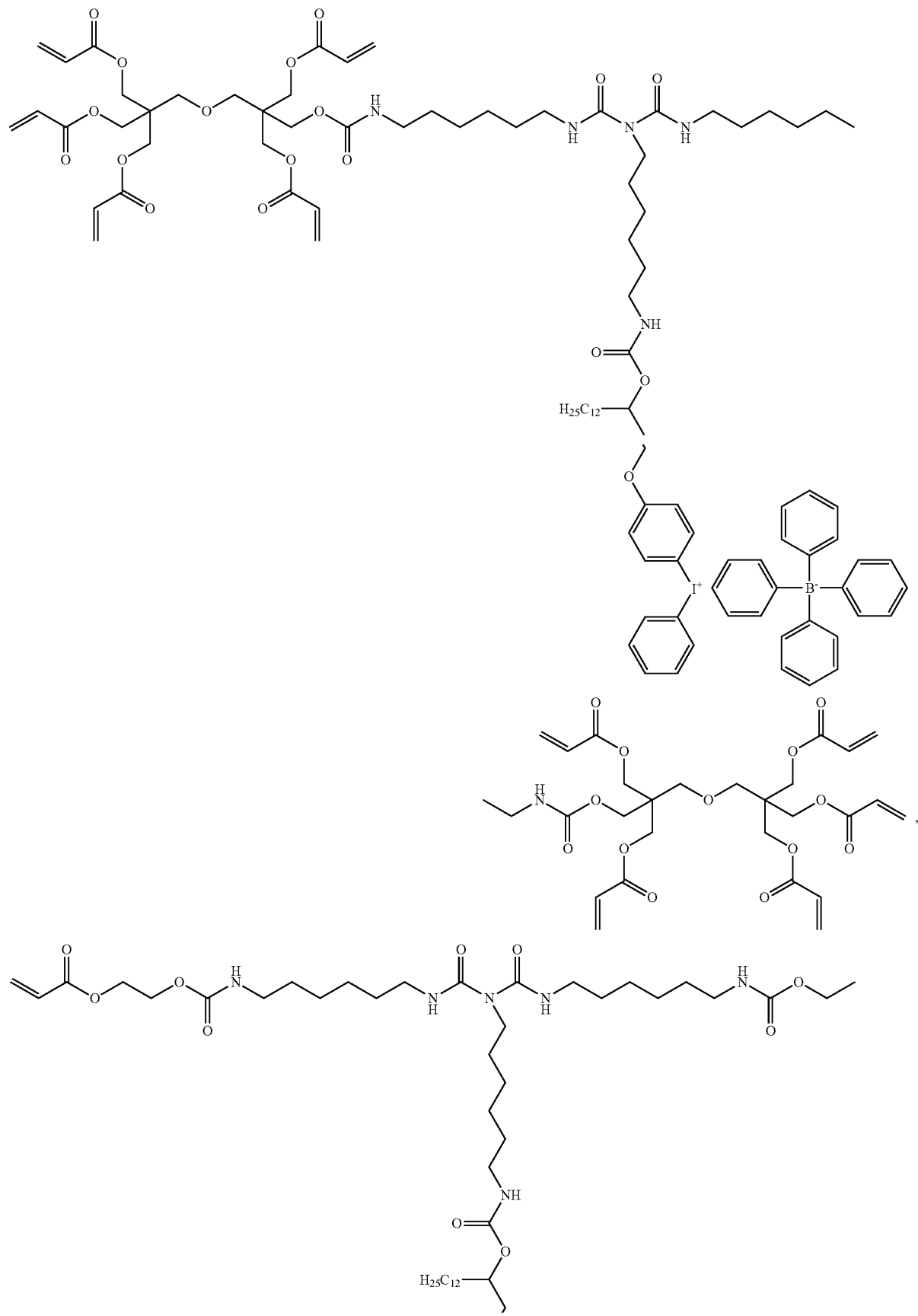

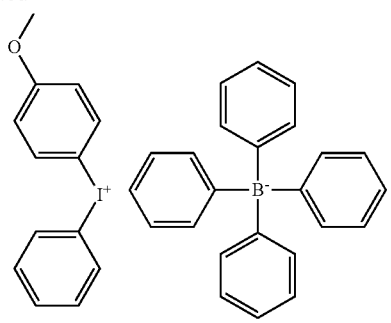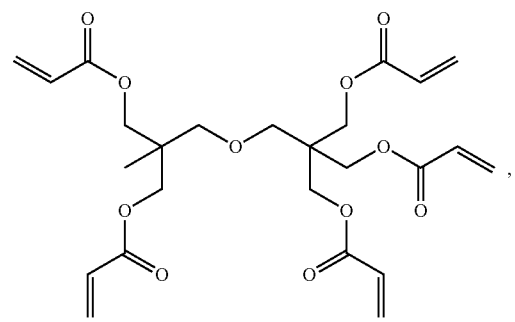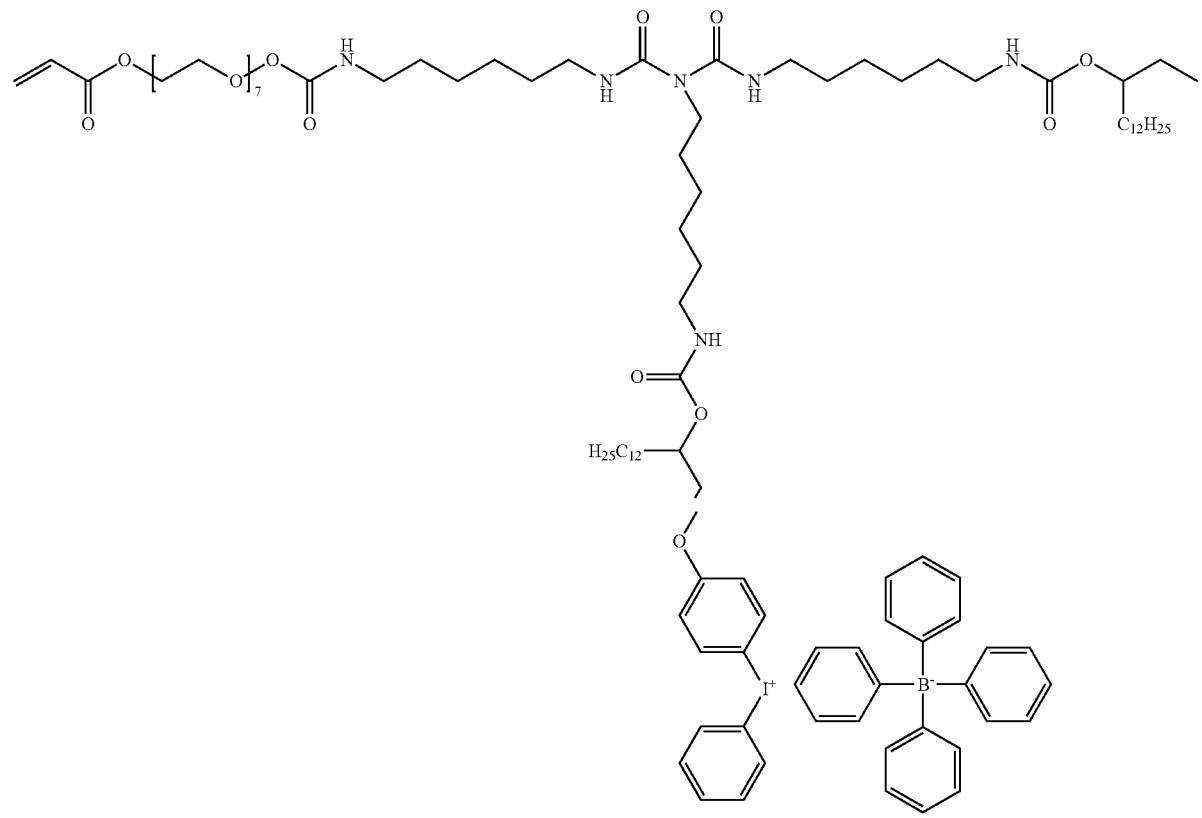

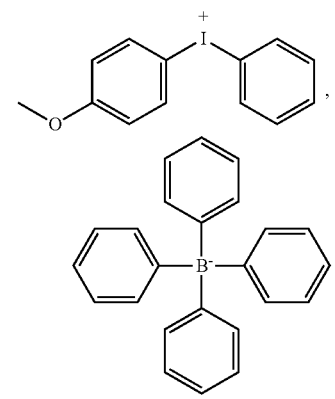
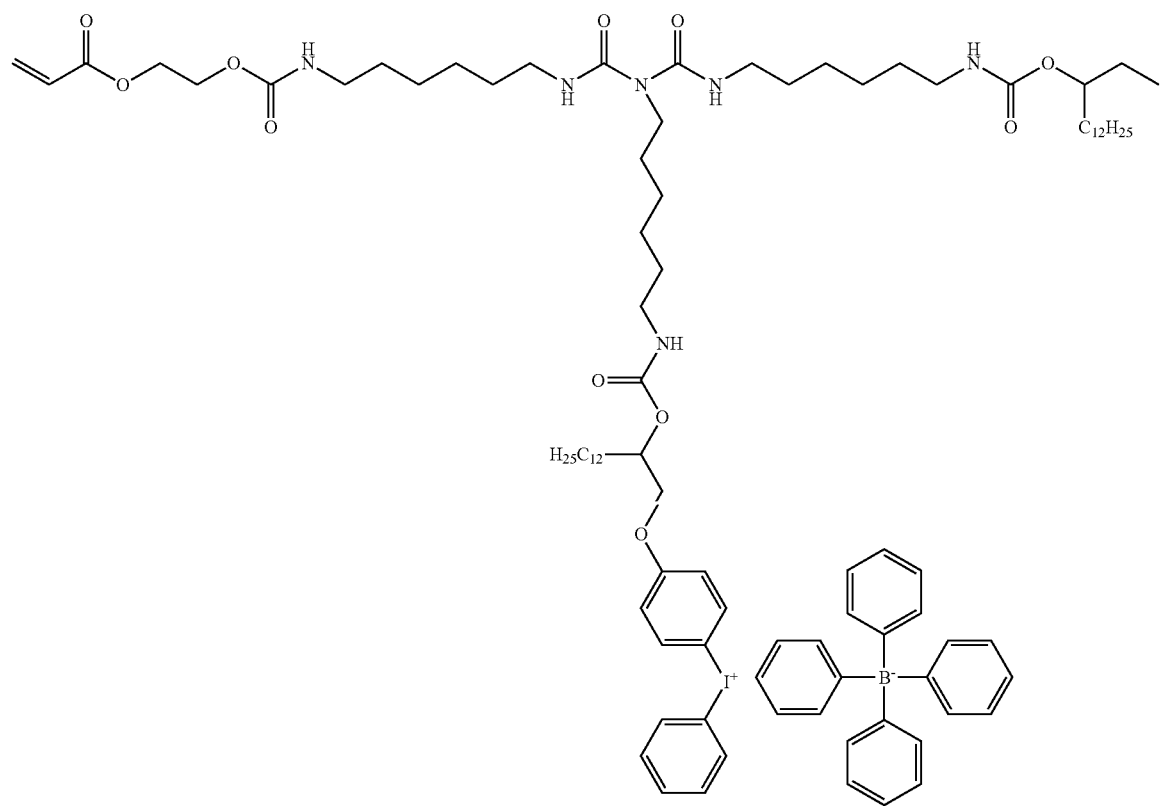
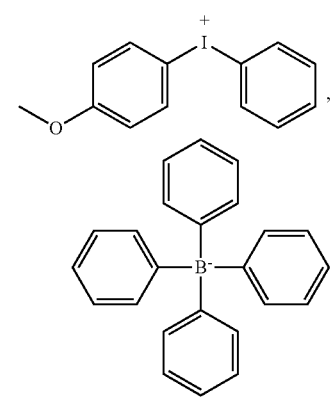

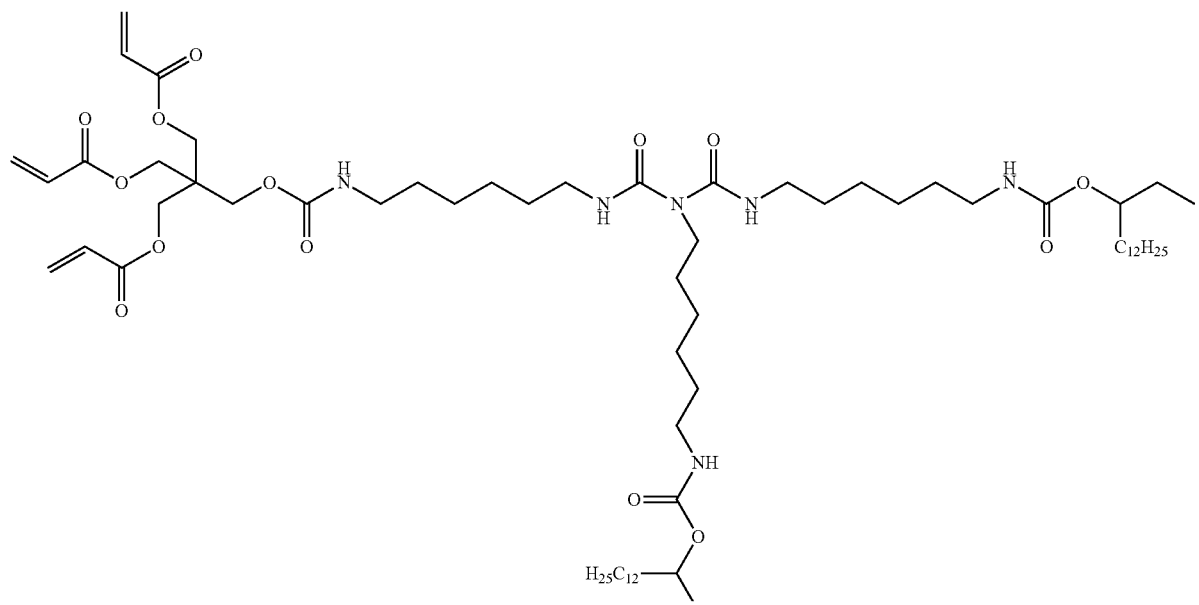
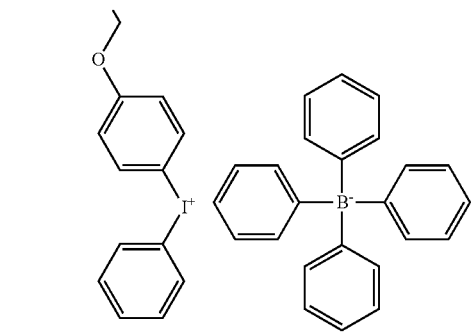
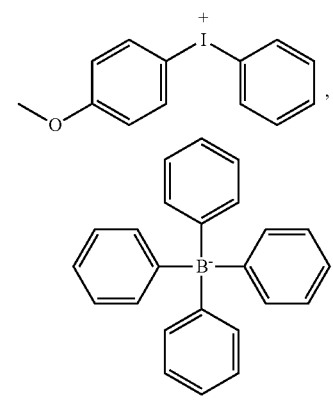

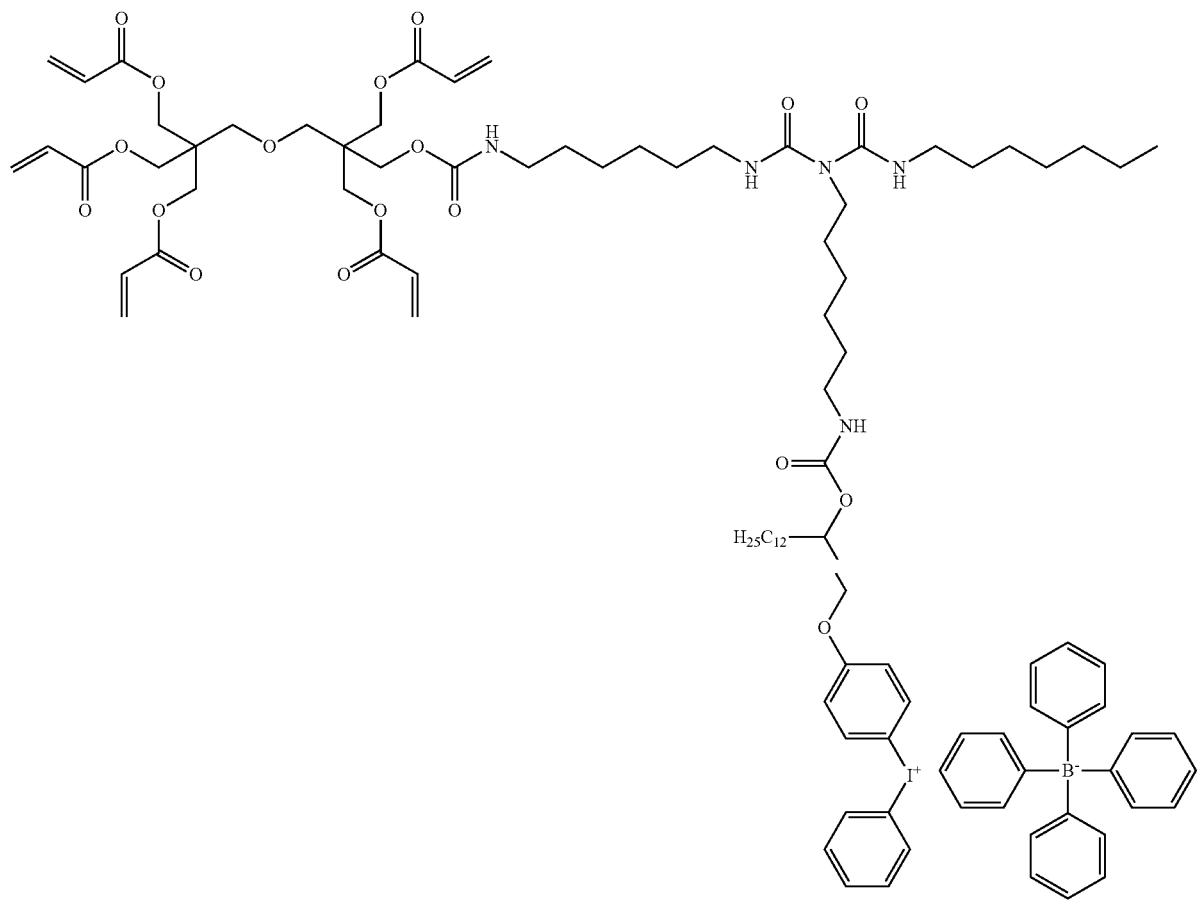
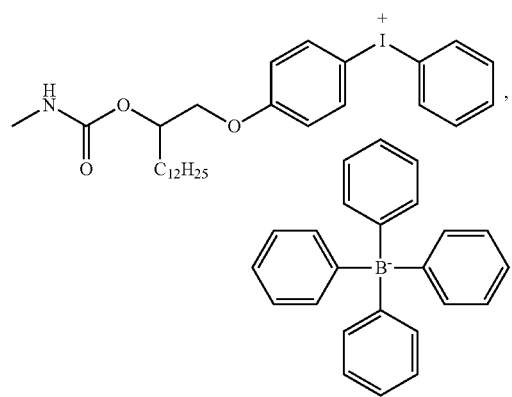

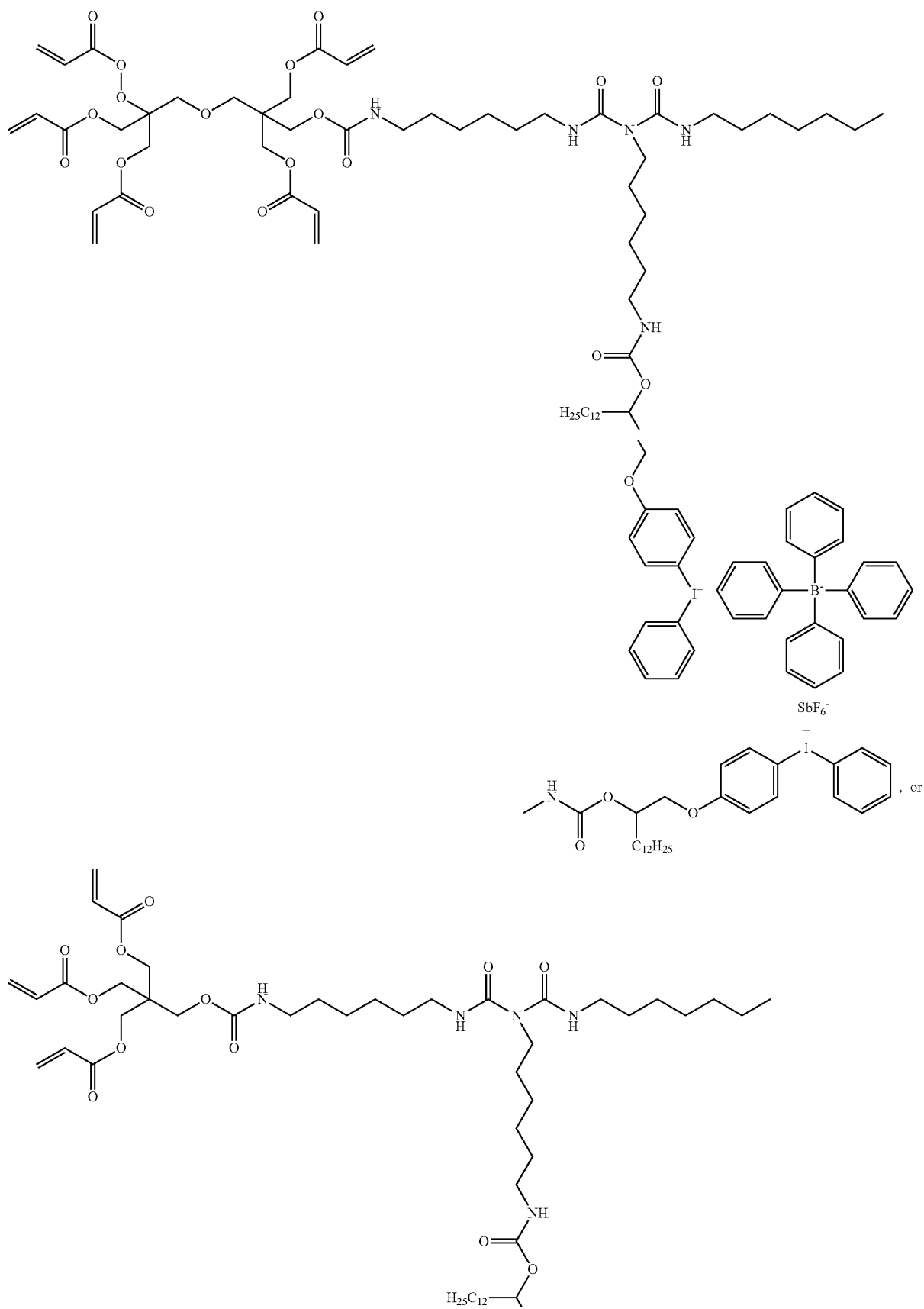

-continued
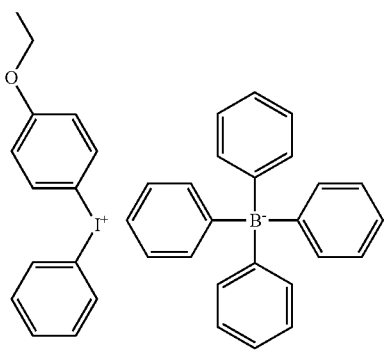
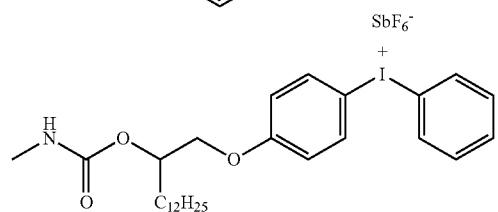
30. The iodonium salt of claim 4 being:
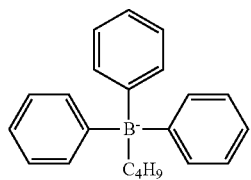
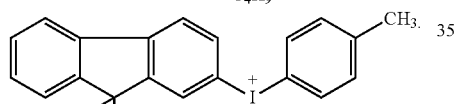
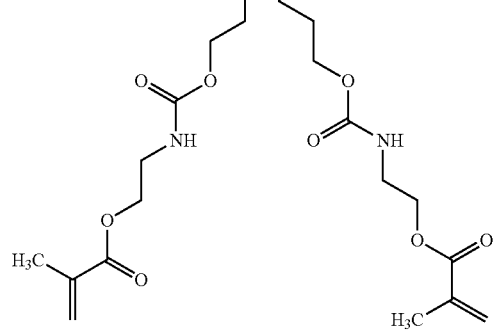
* * * * *